US012751855B2

(12) United States Patent
Lasry et al.

(10) Patent No.: US 12,751,855 B2
(45) Date of Patent: Oct. 6, 2026

(54) SLEEP MONITORING DEVICE

(71) Applicant: iMD Research Inc., Montreal (CA)

(72) Inventors: Nathaniel Lasry, Montreal (CA); Mervyn Gornitsky, Westmount (CA); Hyman Morris Schipper, Côte Saint-Luc (CA); Sharmistha Bhadra, Montreal (CA); Seyedfakhreddin Nabavi, Montreal (CA)

( * ) Notice: Subject to any disclaimer, the term of this patent is extended or adjusted under 35 U.S.C. 154(b) by 830 days.

(21) Appl. No.: 17/299,847

(22) PCT Filed: Dec. 5, 2019

(86) PCT No.: PCT/CA2019/051758
§ 371 (c)(1),
(2) Date: Jun. 4, 2021

(87) PCT Pub. No.: WO2020/113345
PCT Pub. Date: Jun. 11, 2020

(65) Prior Publication Data

US 2022/0117777 A1 Apr. 21, 2022

Related U.S. Application Data

(60) Provisional application No. 62/807,347, filed on Feb. 19, 2019.

(30) Foreign Application Priority Data

Dec. 5, 2018 (CA) ................................ CA 3026695

(51) Int. Cl.

| | |
|---|---|
| ***A61F 5/56*** | (2006.01) |
| ***A61B 5/00*** | (2006.01) |
| ***A61B 7/00*** | (2006.01) |

(52) U.S. Cl.
CPC ............ *A61F 5/566* (2013.01); *A61B 5/4818* (2013.01); *A61B 5/682* (2013.01); *A61B 7/003* (2013.01); *A61F 2005/563* (2013.01)

(58) Field of Classification Search
CPC ......... A61F 5/566; A61B 5/08; A61B 5/4818; A61B 5/682; A61B 7/003
See application file for complete search history.

(56) References Cited

U.S. PATENT DOCUMENTS

| | | | |
|---|---|---|---|
| 5,117,816 | A | 6/1992 | Shapiro et al. |
| 6,089,864 | A | 7/2000 | Strozier |
| 6,092,523 | A | 7/2000 | Skolnik |

(Continued)

FOREIGN PATENT DOCUMENTS

| | | | |
|---|---|---|---|
| EP | 3125836 | B1 | 8/2020 |
| WO | 00/44284 | A2 | 8/2000 |

(Continued)

*Primary Examiner* — Amanda L Steinberg
*Assistant Examiner* — Laura Hodge
(74) *Attorney, Agent, or Firm* — Benoit Yelle; Lavery, de Billy, L.L.P.

(57) ABSTRACT

One general aspect includes an intraoral sleep monitoring device, for determining a status of a user's breathing, including at least one measurement device, on one or more electronics-compatible substrate, adapted to produce data related to a status of a user's breathing and a data storage system recording the data from the at least one measurement device.

7 Claims, 12 Drawing Sheets

(56) References Cited

U.S. PATENT DOCUMENTS

| | | | | |
|---|---|---|---|---|
| 6,766,802 | B1 * | 7/2004 | Keropian | A61F 5/566 128/859 |
| 7,458,810 | B2 | 12/2008 | Bergersen | |
| 10,252,058 | B1 * | 4/2019 | Fuerst | A61N 1/36014 |
| 10,470,847 | B2 * | 11/2019 | Shanjani | A61C 7/002 |
| 2018/0116863 | A1 * | 5/2018 | Shah | A61B 5/02055 |
| 2019/0091061 | A1 * | 3/2019 | Radmand | A61F 5/566 |
| 2019/0099009 | A1 * | 4/2019 | Connor | A61B 5/398 |
| 2019/0099129 | A1 * | 4/2019 | Kopelman | A61B 5/682 |
| 2020/0121492 | A1 * | 4/2020 | McCreery | A61N 1/36078 |

FOREIGN PATENT DOCUMENTS

| | | | | |
|---|---|---|---|---|
| WO | 2010050246 | A1 | 5/2010 | |
| WO | 2013188660 | A2 | 12/2013 | |
| WO | WO-2017201419 | A1 * | 11/2017 | A61B 5/0205 |
| WO | WO-2017218947 | A1 * | 12/2017 | A61B 5/0015 |
| WO | WO-2018044959 | A1 * | 3/2018 | |

* cited by examiner

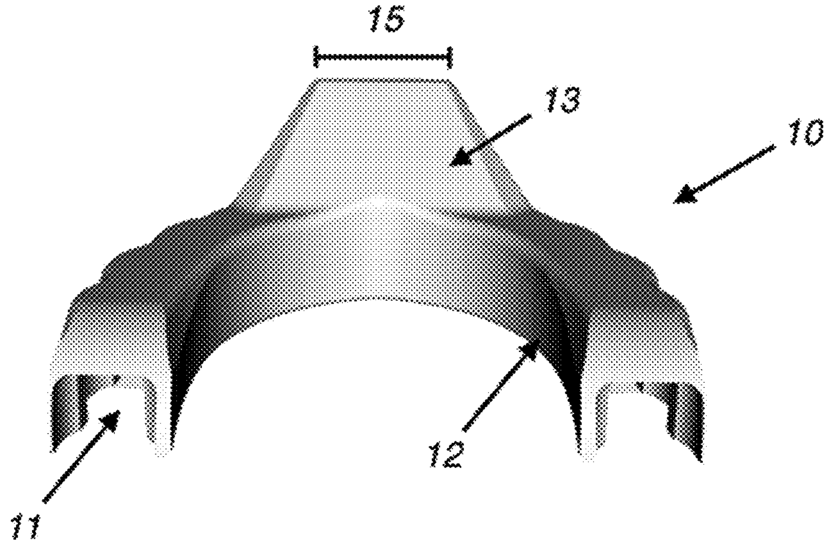
FIG 7
FIG 8
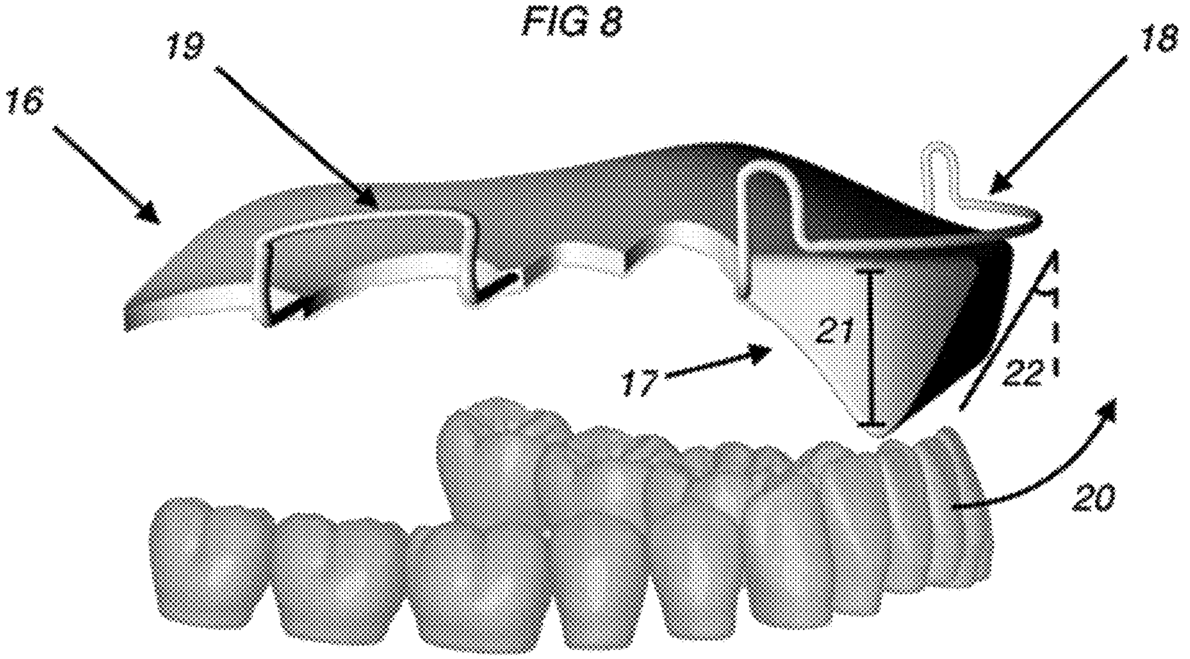

SLEEP MONITORING DEVICE

CROSS REFERENCE TO RELATED APPLICATIONS

This non-provisional patent application is a U.S. National Phase of International Patent Application PCT/CA2019/051758, filed Dec. 5, 2019, which is hereby incorporated by reference in its entirety and which claims priority based upon the prior U.S provisional patent application entitled "INTRAORAL DATA-TRACKING DEVICE", application No. 62/807,347, filed Feb. 19, 2019, in the name of iMD Research Inc., and based upon the prior Canadian patent application entitled "SINGLE ARCH DEVICE FOR GRADUAL MANDIBULAR ADVANCEMENT", application number 3,026,695, filed Dec. 5, 2018, in the name of iMD Research Inc., both of which being herein included by reference in their entirety.

TECHNICAL FIELD

The present invention relates to a monitoring device and, more particularly, to sleep monitoring device.

BACKGROUND

Obstructive Sleep Apnea (OSA) is a condition where patients have recurring episodes of decrease or cessation of breathing (i.e., hypopnea or apnea) when they sleep that is caused by an obstruction of the upper respiratory tract. While current estimates place the prevalence of OSA at 13% of males and 6% of females, prevalence rates continue to increase because of rising levels of obesity. Indeed, 40% of patients with obesity have OSA. Conversely, 70% of patients with OSA are obese.

In order to diagnose patients with OSA, bulky and cumbersome solutions exist (polysomnography apnea testing system, cardiorespiratory polygraphy apnea testing system, etc.). These devices are used punctually, generally during a single night, to detect whether a patient has the signs and symptoms of OSA.

In order to provide relief to patients with OSA, bulky and cumbersome solutions exist such as Continuous Positive Airway Pressure (CPAP) devices, Bilevel Positive Airway Pressure (BiPAP), dual-arch Mandibular advancement devices (MAD), etc. These therapeutic devices do not monitor the parameters measured in diagnostic tests and hence cannot objectively determine the course of the illness or monitor the effectiveness of the treatment.

The present invention addresses the need for an improved device that can diagnose, monitor and/or treat sleep relevant at least to OSA.

SUMMARY

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One general aspect includes an intraoral sleep monitoring device, for determining a status of a user's breathing, including at least one measurement device, on one or more electronics-compatible substrate, adapted to produce data related to a status of a user's breathing; and a data storage system recording the data from the at least one measurement device.

Implementations may include one or more of the following features. The sleep monitoring device may further include an intraoral frame adapted to removably attach to a dental arch of a user and the intraoral frame may also be adapted to hold at least one intraoral flexible substrate of the electronics-compatible substrates. The sleep monitoring device may also additionally include a wristband frame adapted to hold at least one wristband substrate of the electronics-compatible substrates. The at least one measurement device may further be selected from one or more of a sound sensor, a photoplethysmogram sensor, a pressure transducer, a temperature sensor, an electroencephalography probe, a gyroscope, an electrocardiogram and a blood chemical sensor. The device may also further include a signal treatment module to filter out irrelevant data from data collected by the at least one measurement device. The device may yet also further include a memory module for storing data from the at least one measurement device. A storage system may also be further provided for storing data from the at least one measurement device. A network interface module may further enable distribution of the control module into distinct physical enclosures. The device may be produced using a single compound by additive manufacturing or by milling. The at least one measurement device may further include a sound sensor that determines the status of the user's breathing by measuring an intraoral noise of the user. The control module may further compute, in real-time, the adjustment distance to minimize the user's intraoral noise.

One general aspect includes a mandibular advancement device including an intraoral frame adapted to removably attach to a dental arch of a user; a protrusive wedge element, at an anterior portion of the intraoral frame, adapted to cause the lower mandible to slide forward on an adjustment distance on occlusion, the adjustment distance being settable between a minimum distance and a maximum distance; at least one measurement device adapted to produce data related to a status of the user's breathing; and a data storage system recording the data from the at least one measurement device.

Implementations may include one or more of the following features. The protrusive wedge element may extend away from a basis of the intraoral frame by about 12 mm. Recessed impressions of teeth of a facing arch may be reproduced on a portion of the protrusive wedge element facing the teeth for enhanced comfort. A retention mechanism fastening the device to the teeth may be similar to an occlusal splint. A retention mechanism fastening the device to the teeth may alternatively be a palatal base plate with metal clasps. The protrusive wedge element may extend away from a basis of the intraoral frame by between 6-18 mm. The protrusive wedge element extending away from a basis of the intraoral frame may have a base width of about 25 mm. The protrusive wedge element extending away from a basis of the intraoral frame may have a base width of between 15-35 mm. The protrusive wedge element extending away from a basis of the intraoral frame may be angled toward teeth of a facing arch by between 30-60 degrees.

One general aspect includes a dynamic mandibular adjustment device including a double-arch intraoral frame adapted to removably attach to dental arches of a user; a bloc element adapted to cause the lower mandible to slide forward on an adjustment distance, the adjustment distance being settable between a minimum distance and a maximum distance; at least one measurement device adapted to determine a status of the user's breathing in real-time priority processing; a control module adapted to compute, in real-time priority processing, the adjustment distance between the minimum distance and the maximum distance upon modification of the status of the user's breathing; and a mechanical actuator adapted to cause the bloc element to set the adjustment distance on instructions from the control module.

Implementations may include one or more of the following features. The control module may further include a microcontroller allowing a remote control of the mechanical actuator. The mechanical actuator may set the adjustment distance by converting energy into a mechanical modification of the bloc element based on one or more of a piezoelectric effect, an electrostatic effect, an electromagnetic effect, a hydraulic effect and shape-memory alloy properties. The mechanical actuator may be a microelectromechanical system (mems).

One general aspect includes a method for repositioning a user's mandible including determining, in real-time priority processing, a user's breathing status from acquired data related thereto; computing, in real-time priority processing, an adjustment distance between a minimum distance and a maximum distance and setting the adjustment distance by causing the mandible to slide.

Implementations may include one or more of the following features. The acquired data may be related to intraoral noise. The adjustment distance may be computed to minimize the user's intraoral noise. The method may further include treating the acquired data to filter out irrelevant data. The protrusive wedge element may descend from the anterior portion of the device by about 12 mm. The protrusive wedge element descending from the anterior portion may include recessed impressions of lower teeth in the forward facing portion of the protrusive wedge element for enhanced comfort. The single-arch gradual mandibular advancement device may be produced using a single compound by additive manufacturing. The single-arch gradual mandibular advancement device may further comprise a retention mechanism fastening the device to the teeth similar to an occlusal splint. Alternatively, the single-arch gradual mandibular advancement device may further comprise a retention mechanism fastening the device to the teeth in the form of a palatal base plate with metal clasps. The protrusive wedge element may descend from the anterior portion of the device by between 6-18 mm. The protrusive wedge element descending from the anterior portion of the device may have a base width of about 25 mm. The protrusive wedge element descending from the anterior portion of the device may have a base width of between 15-35 mm. The protrusive wedge element descending from the anterior portion of the device may be inwardly angled at between 30-60 degrees.

One general aspect includes a single-arch gradual mandibular advancement device including a dental splint attached to a mandibular teeth that is tailored to a user for customized retention, where the single-arch device is adapted to fit only a lower teeth of the user. The single arch gradual mandibular advancement device also includes a protrusive wedge element, ascending from an anterior portion of the dental splint, adapted to cause the lower mandible to slide forward on occlusion to open the upper respiratory tract. The device prevents full occlusion and maintains a separation between the user's upper and lower posterior teeth for preventing clenching.

Implementations may include one or more of the following features. The protrusive wedge element may ascend from the anterior portion of the device by about 12 mm. The protrusive wedge element ascending from the anterior portion of the device may include recessed impressions of upper teeth in the backward facing portion of the protrusive wedge element for enhanced comfort. A retention mechanism may be provided for fastening the device to the teeth similarly to an occlusal splint. A retention mechanism may be provided for fastening the device to the teeth in the form of a palatal base plate with metal clasps. The protrusive wedge element may ascend from the anterior portion of the device by between 6-18 mm. The protrusive wedge element ascending from the anterior portion of the device may have a base width of about 25 mm. The protrusive wedge element ascending from the anterior portion of the device may have a base width of between 15-35 mm. The protrusive wedge element ascending from the anterior portion of the device may be outwardly angled at between 30-60 degrees.

BRIEF DESCRIPTION OF THE DRAWINGS

Further features and exemplary advantages of the present invention will become apparent from the following detailed description, taken in conjunction with the appended drawings, in which:

FIG. 7 is a posterior view of the single-arch lower mandibular device in accordance with the teachings of the present invention;

FIG. 8 is an isometric lateral view of the single-arch palatal base plate with metal clasps in accordance with the teachings of the present invention;

DETAILED DESCRIPTION

Figure 1:
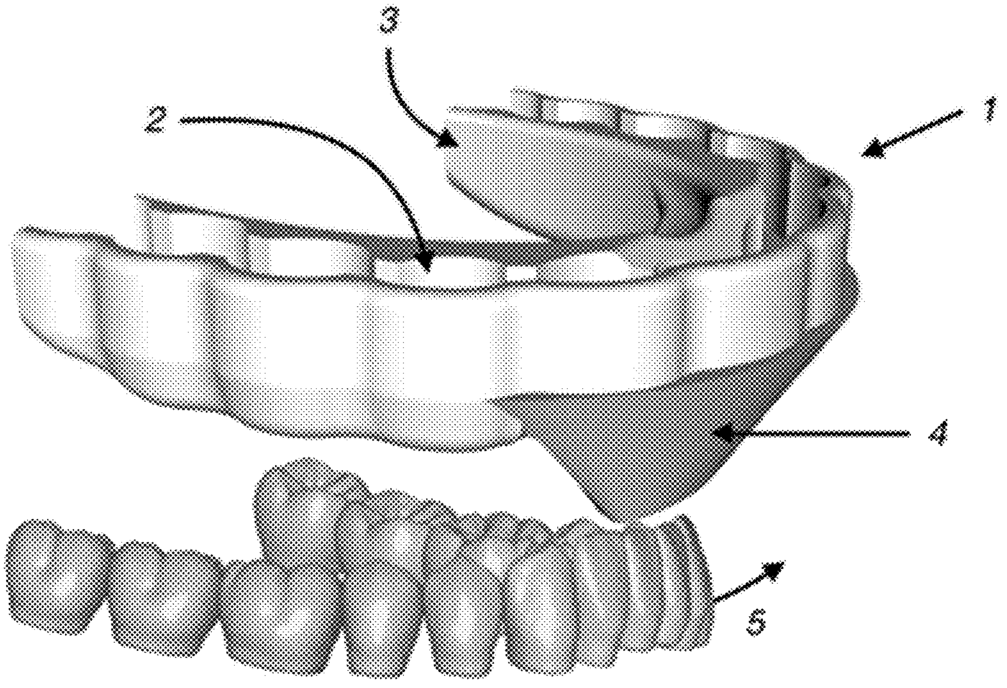
FIG. 1 is an isometric view of a single-arch maxillary device in accordance with the teachings of the present invention.

The present invention relates to a sleep monitoring device that, in a first set of embodiments, can be used to provide at least some of the data helpful for specialists in the diagnosis of Obstructive Sleep Hypopnea (OSA), Central Hypopnea or other sleep disorders. It has been shown that the same data can also be helpful to other medical specialists, physical trainers or the wearer in other contexts such as tracking of the wearer's health and performance indicators in multiple contexts, including during sports sessions (e.g., tracking of heart performance, tracking of concussions, etc.), during medical interventions, or to monitor patients at risk of cardiovascular events etc. The present invention also relates to an intraoral medical device that, in a second set of embodiments, can be used as a partial or complete treatment of OSA in addition to providing of the helpful data on the effectiveness of the treatment and the progression of the disease. In a third embodiment, the intraoral medical device can be adjusted, by an actuator in real time, during the patient's treatment progress. In some embodiments, the intraoral medical device may be manufactured using additive manufacturing techniques in local dental labs. In other embodiments, the intraoral medical device is produced by milling during manufacture. The present invention also relates, in a fourth set of embodiments, to a method for treating the data, produced in any of the three previous sets of embodiments, to extract desired characteristics of a signal related to the user's health making it helpful for medical specialists to interpret the ensuing data.

In order to diagnose OSA, a polysomnography test may be performed at a sleep clinic. The patient is provided with a bedroom equipped with an audiovisual system for diagnostic purposes and to ensure safety. The sleep of the patient is observed throughout the night for recording the data. Several sensors must be applied to the patients scalp, temples, hands, chest and legs. While the sensors are designed not to cause pain and limit movements during the night, temporary skin irritation may be observed where sensors were applied to the skin. The sensors aim at recording electrical brain activity, eye movements, muscle tone, heart rate, breathing movements, blood oxygen levels, body position, limb movements and snoring.

Cardiorespiratory polygraphy may also be done by the patient at home with a portable device. The device comprises multiple sensors to be installed by the patient and is meant to record chest and abdominal effort, heart rate, body position, nasal flow, snoring and oxygen in the blood.

The data that may be taken into account during the diagnosis of OSA is typically organized over time. Different tools may be used to obtain such data. The following list provides examples of data and tools associated therewith:

Blood oxygen saturation obtained from an SpO2 probe.

Oxygen desaturation obtained from the SpO2 probe.

Pulse (e.g., Beats per Minute (BPM)) obtained from the SpO2 probe.

Heart performance data obtained from chest probes

Inductive Abdominal Effort data obtained from chest probes.

Patient respiratory oral and nasal airflow obtained from nasal tubes.

Snoring data obtained from one or more microphones.

Body position data obtained through human observation and EMG (electromyogram) probes on the patient's limbs.

Patient event data obtained directly from the patient.

Rapid eye movement (REM) data obtained from temporal probes (electrooculography).

Sleep status data obtained from EEG (Electroencephalography) scalp probes.

Bruxism data from EMG (Electromyogram) probes on the patient's jaw and microphone(s).

From the data obtained from the various tools, different measurements and indexes may be derived. Oxygen desaturation index (ODI), Respiratory disturbance index (RDI) and Apnea-Hypopnea Index (AHI) may be determined from analysis of the data. Control of ventilatory patterns (or respiratory drive pattern) may also be analyzed. For instance, it is possible to identify a Cheyne-Stokes respiration pattern from the data, which may in turn help specialists in the diagnosis of Obstructive Hypopnea, Central Hypopnea or other sleep disorders.

Reference is now made to the drawings. In accordance with the first set of embodiments, an sleep monitoring device 1100 is provided as depicted in FIG. 11 to FIG. 14 and FIG. 19. The sleep monitoring device 1100 may be used as a diagnostic aid in the context of different illnesses (apnea, cardiovascular monitoring, etc.). The sleep monitoring device 1100 comprises an electronics module 1110. In one embodiment, the sleep monitoring device 1100 is configured to be produced by additive manufacturing techniques (e.g., 3D printing). In another embodiment, the sleep monitoring device 1100 is milled out of a bloc. The sleep monitoring device 1100 may therefore be made of a single compound. The electronics module 1110 may be integrated within the sleep monitoring device 1100 at the time of manufacturing (e.g., as printable electronics, as a separate module (e.g., CMOS chip) or a combination thereof) or the sleep monitoring device 1100 may be configured to receive the electronics module as an add-on module. The electronics module 1110 may also be distributed in a plurality of submodules (not shown). The submodules may be in wireless communication with one another (e.g., using Bluetooth, proprietary protocol, etc.). The submodules may also be connected with one another at the time of manufacturing (e.g., using wires or using additive conductive material to build the necessary connections).

In some embodiments, the monitoring device 1100 may be embodied in a single-arch sleep monitoring device on which one or more measurement devices may be mounted, to be worn by the user during sleep. The sleep monitoring device 1100 may also alternatively be embodied as, or otherwise further comprise, a wristband on which one or more of the measurement devices may be mounted, to be worn by the user during sleep. The wristband and/or the single-arch sleep monitoring device may be produced by additive manufacturing techniques (e.g., 3D printing) or by milling. The wristband and/or the single-arch sleep monitoring device of the sleep monitoring device 1100 may therefore be made of a single compound. The wristband and/or the single-arch sleep monitoring device of the sleep monitoring device 1100 may be produced on a flexible substrate. In the case where the sleep monitoring device

1100 comprises a single-arch sleep monitoring device and a wristband, the wristband may be configured to be able to bind and attach to the intraoral single-arch sleep monitoring device.

The one or more measurement devices may be positioned at different locations on or within the sleep monitoring device 1100. Openings 1120 may be provided in the sleep monitoring device 1100 where one or more of the different measurement devices may be positioned when direct contact with the wearer is required. Skilled persons will readily recognize that different measurement devices have different requirements and be able to properly determine the best position for such devices. When receiving electrodes (e.g., such as for EEG measurements) may be placed on the soft palate, but preferably placed directly on bone (like when placed on the scalp). The soft palate typically begins where the anterior palatal bone ends and the muscular portion of the palate begins. This typically consists of the posterior third of the palate. When using three different EEG probes, each could be positioned within 1 cm to 4 cm from each other. The position of the probes should be determined considering the laryngeal spasm (or gag reflex), which is typically triggered by touching the roof of the mouth, the back of the tongue, the area around the tonsils, the uvula, and the back of the throat. Alternatively, the EEG electrodes could be placed in contact with the inner part of the upper front lip to collect data from the frontal regions of the brain that are most active during REM (Rapid Eye Movement) sleep.

The electronics module 1110 may be connected to one or more measurement devices mounted on or integrated within the sleep monitoring device 1100. The electronics module 1110 may also, alternatively or additionally, comprise one or more measurement devices integrated therein. The electronics module 1110 also comprises a memory module for storing data from the one or more measurement devices. The electronics module 1110 also comprises or is connected to a sealed a power source. The power source may be mounted or integrated within sleep monitoring device 1100 or directly within the electronics module 1110. In some embodiments, the power source is rechargeable (wirelessly rechargeable batteries; gyroscope-based rechargeable batteries; solar-power rechargeable batteries), but it may also be a single charge battery. In some embodiments, the sleep monitoring device 1100 comprises a charging port (on the electronics module 1110 or elsewhere).

In some embodiments, the sleep monitoring device 1100 may comprise a part in which a plurality of sensors are integrated.

The one or more measurement devices may comprise a photoplethysmogram (PPG) sensor mounted on the sleep monitoring device 1100 facing the palate of the wearer, such that the PPG sensor is in contact or close proximity with one or more blood vessels of the wearer. The PPG sensor can be used to measure blood O2 levels, heart rate and may further provide basic data to extract respiratory rate and blood pressure. The data produced by a plurality of photoplethysmogram (PPG) sensors and a Pulse Transit Time (PTT) may be combined to compute the blood pressure in real time. In some embodiments, necessary electrical connectivity between the PPG sensor and the electronics module 1110 are added during the manufacturing step (e.g., as wires or as 3D printable conductive material). In other embodiments, the PPG sensor is in wireless communication with the electronics module 1110 (e.g., Bluetooth, proprietary protocol, etc.).

The one or more measurement devices may comprise a pressure transducer or a pressure switch integrated in the electronics module 1110 or mounted on or integrated within (a non-airtight compartment of) the sleep monitoring device 1100. The pressure transducer or a pressure switch can be used to measure variations in intraoral air pressure to indicate respiratory frequency and/or occlusal pressure, which could be useful to monitor bruxism. In some embodiments, necessary electrical connectivity between the pressure transducer or a pressure switch and the electronics module 1110 are added during the manufacturing step (e.g., as wires or as 3D printable conductive material). In other embodiments, the pressure transducer or a pressure switch is in wireless communication with the electronics module 1110 (e.g., Bluetooth, proprietary protocol, etc.).

The one or more measurement devices may comprise a temperature sensor integrated in the electronics module 1110 or mounted on or integrated within the sleep monitoring device 1100. The temperature sensor can be used to measure variations in user's temperature. In some embodiments, necessary electrical connectivity between the temperature sensor and the electronics module 1110 are added during the manufacturing step (e.g., as wires or as 3D printable conductive material). In other embodiments, the temperature sensor is in wireless communication with the electronics module 1110 (e.g., Bluetooth, proprietary protocol, etc.).

The one or more measurement devices may comprise EEG (Electroencephalography) probes, such as the examples depicted on FIG. 15, may be mounted on or integrated within (e.g., at the openings 1120) the sleep monitoring device 1100. The EEG probes can be used to measure electroencephalography data. In some embodiments, necessary electrical connectivity between the EEG probes and the electronics module 1110 are added during the manufacturing step (e.g., as wires or as 3D printable conductive material). In other embodiments, the EEG probes is in wireless communication with the electronics module 1110 (e.g., Bluetooth, proprietary protocol, etc.).

The one or more measurement devices may comprise one or more accelerometer and/or gyroscope sensors integrated in the electronics module 1110 or mounted on or integrated within the sleep monitoring device 1100. The one or more accelerometer and/or gyroscope sensors can be used to measure head movements and body vibrations of the wearer. The head movements and body vibrations indicate the wearer's sleep state (e.g. awake, REM sleep, light sleep, deep sleep). Similarly, the head movements and body vibrations of the wearer may then be used to extrapolate restless leg syndrome and other movement-based sleep disorders. In some embodiments, necessary electrical connectivity between the one or more accelerometer and/or gyroscope sensors and the electronics module 1110 are added during the manufacturing step (e.g., as wires or as 3D printable conductive material). In other embodiments, the one or more accelerometer and/or gyroscope sensors is in wireless communication with the electronics module 1110 (e.g., Bluetooth, proprietary protocol, etc.). The head movements and body vibrations of the wearer may then be used to extrapolate restless sleep and other movement-based disorders.

The one or more measurement devices may comprise electrocardiogram (EKG or ECG) probes, such as the examples depicted on FIG. 15, may be mounted on or integrated within (e.g., at the openings 1120) the sleep monitoring device 1100. The ECG probes can be used to measure heart performance data. In some embodiments, necessary electrical connectivity between the ECG probes and the electronics module 1110 are added during the manufacturing step (e.g., as wires or as 3D printable conductive material). In other embodiments, the ECG probes is in wireless communication with the electronics module 1110 (e.g., Bluetooth, proprietary protocol, etc.). The ECG probes may, for instance, take the form of small microelectromechanical systems (MEMS).

The one or more measurement devices may comprise a sound sensor integrated in the electronics module 1110 or mounted on or integrated within the sleep monitoring device 1100. The sound sensor can be used to measure variations in sound (e.g., intensity of snoring noise and breathing effort). In some embodiments, necessary electrical connectivity between the sound sensor and the electronics module 1110 are added during the manufacturing step (e.g., as wires or as 3D printable conductive material). In other embodiments, the sound sensor is in wireless communication with the electronics module 1110 (e.g., Bluetooth, proprietary protocol, etc.).

The one or more measurement devices may comprise a blood-chemical sensor integrated in the electronics module 1110 or mounted on or integrated within the sleep monitoring device 1100. The blood-chemical sensor can be used to measure variations in blood levels of one or more chemicals present in the wearer's blood. In some embodiments, necessary electrical connectivity between the blood-chemical sensor and the electronics module 1110 are added during the manufacturing step (e.g., as wires or as 3D printable conductive material). In other embodiments, the blood-chemical sensor is in wireless communication with the electronics module 1110 (e.g., Bluetooth, proprietary protocol, etc.). Examples of blood chemical that may be measured include cortisol and glucose. Other biomarkers that fluctuate during sleep may be measured and can indicate important information with respect to sleep disorders.

In accordance with the second set of embodiments, one or more measurement devices (as discussed with reference to the first set of embodiments) may be integrated into a mandibular advancement device that fits a single arch. The mandibular advancement device is designed to treat obstructive sleep apnea (OSA), snoring, bruxism, temporomandibular discomfort and gastroesophageal reflux (GERD). Example of sensors and measurement devices include PPG probe, ECG probe, EEG probe, pressure sensor, temperature sensor, sound sensor, accelerometer and/or gyroscope, etc. similar or identical to the same sensors and measurement devices discussed with reference to the first set of embodiments.

The intraoral device is of low bulk because it fits a single arch, leaving the remaining arch unconstrained. This mandibular advancement device gradually moves the lower mandible forward on occlusion by sliding the mandible along the inverted wedge element. The user's upper respiratory tract is gradually opened on occlusion as the lower mandible slides forward along the wedge element. The increase the diameter of the upper respiratory tract facilitates the passage of air into the lungs and treats underlying conditions such as OSA, snoring, bruxism, temporomandibular discomfort and GERD. Mandibular advancement is gradual on occlusion and thus avoids the application of constant and sustained tension on the temporomandibular joint (TMJ) that is known to cause long-term complications.

In accordance with the second set of embodiments, an intraoral single-arch gradual mandibular advancement device to be worn during sleep to open the upper respiratory tract and treat OSA, snoring, bruxism, temporomandibular discomfort and GERD is discussed. This second set of embodiments substantially eliminates or reduces disadvantages associated with prior devices that need to engage both dental arches, leading to greater bulkiness and discomfort. The second set of embodiments also substantially eliminates or reduces other disadvantages of dual-arch MADs such as the associated complications that arise from the sustained pressure they exert on the temporomandibular joint. This single-arch gradual MAD uses an inverted wedge element to gradually slide the lower mandible forward on occlusion. It does not have multiple components that are prone to collecting pathogens in the interstices between the components nor does it require the assembly of device components outside of a dental lab because it can be locally produced by additive manufacturing.

In particular, an intraoral mandibular advancement device is shown to treat disorders that result from the obstruction of the upper respiratory tract such as OSA, snoring, bruxism, temporomandibular discomfort and GERD. The device can be manufactured as a single piece that includes a protruding wedge element that projects out of the anterior portion of the device at the apex of the arch and causes the lower mandible of the user to advance on occlusion. This results in the expansion of the upper respiratory tract or in a decrease in the obstruction thereof. This protruding wedge element intercepts the opposing teeth on occlusion and slides the lower mandible forward by having the teeth slide forward along the wedge. The protruding wedge element thus prevents normal occlusion, slides the lower mandible forward, thereby opening the upper respiratory tract. By preventing normal occlusion, the device also maintains a separation between the upper and lower arches that prevent clenching. It is important to note that, as a single arch device, the lower mandible is never fully constrained, has full mobility in all directions and prevents sustained tension on the temporomandibular joint.

In some embodiments, the electronics module 1110 discussed with reference to the first set of embodiments may be provided with the intra-oral device from the second set of embodiments. In certain embodiment, the electronics module 1110 and/or the one or more measurement devices may be positioned in the wedge element.

In certain embodiment, the wedge element is an add-on module that can supplement the sleep monitoring device depicted with reference to the first set of embodiments. The add-on wedge module may be fixed to the original device by way of pre-existing mutually cooperating mechanical features (e.g., cooperating clasps, sliding channels, etc.) or may be glued in place. Advantageously, the addition of the add-on wedge module to the original device may be performed by the end user without requiring professional interventions. In certain embodiments, different add-on wedge modules may be provided with different slopes as a means to allow adaptation to the wearer (e.g., sloped increasing between the module to be worn over a period of time). In certain embodiments, the slope of the wedge can be automatically adjusted (e.g., through hydraulic and/or mechanical actuators in the wedge) considering measurements taken from the wearer. In some embodiments, the slope adjustment may be performed while the user sleeps considering current measurements from the wearer and/or wearing time, e.g., to increase wearing comfort for the wearer.

To produce the device, alginate, silicon or digital impressions are taken of the user's upper and lower arches as well as a bite registration and a protrusive impression of the lower mandible. The mandibular advancement device is customized to the impression of the user's upper teeth for optimal fit and retention. Impressions of both arches, bite registration and protrusive impression of the lower mandible are used to design the dimensions of the device and the protrusive wedge element. When impressions of both arches are used, impression of one arch will allow customization of the retention mechanism while the impression of the other arch will enable the proper fit of the device on occlusion. The bite registration may be used to determine the position of the protrusive wedge element and make sure that on occlusion, the user's teeth will occlude onto the protrusive wedge, without occluding behind it. Finally, the protrusive impression enables the incline to push the lower mandible forward up to its maximal possible protrusion on full occlusion.

Specifically, the protruding wedge element has a length-to-height ratio that depends on the length of maximum possible advancement of the user's lower mandible. The height of the wedge is standardized to values ranging between 10-15 mm. The length of the wedge element may be determined by using the distance between the bite registration taken in normal occlusion and the bite registration for the maximal protrusion of the lower mandible. The user should not be able to occlude without the lower teeth engaging the wedge element. Hence, the angle of the wedge is determined by this length-to-height ratio. Typical forward movement of lower mandibles range between 8 and 12 mm and hence will result in a wedge element of dimensions ranging between 8 and 12 mm in width and 10 and 15 mm in height protruding outwardly from the main body of the device. The lower arch impression is also used to produce an impression of the lower incisors on the anterior facing part of the protruding wedge element. The lower mandible is gradually engaged on occlusion and progressively opens the upper respiratory tract.

Specifically, a mandibular advancement device is provided, in accordance with the second set of embodiments, that gradually advances the lower mandible and can consist of materials that provide the required requisite strength and flexibility such as metals like titanium, nickel and stainless steel and polymers such as acrylic, elastomeric or polymeric materials, as well as rubbers, silicones, vinyls, hard plastic, thermoplastic, thermosensitive acrylic resin, natural materials and combinations thereof. While in one embodiment of the present invention the use of metal is present, the preferred embodiment features a single continuous piece of polymer that molds around the teeth of the user with a protruding wedge element that intercepts the lower teeth on occlusion. The device gradually advances the user's lower mandible forward on occlusion to eliminate or reduce sleep disorders such as OSA, snoring, bruxism, temporomandibular discomfort and GERD. The advancement distance is settable between a minimum distance and a maximum distance. Specifically, the optimum amount of offset of the lower jaw varies with each user and is therefore customized for each user.

To avoid prolonged tension and discomfort, the lower jaw is not actively advanced and locked into a protruding position. Four sets of impressions are taken to customize the fit of the device to the user and also to ensure comfort while acting to advance the lower mandible gradually. Given that retention mechanisms that hold a device firmly in place are paramount in all intraoral devices, the device is designed to withstand the user's ordinary movements without falling. Three mechanisms for the retention of the intraoral device are displayed in the figures of the preferred embodiments and include a dental maxillary mold, a lower mandibular mold and a palatal base plate with metal clasps retaining the anterior and posterior teeth.

The device prevents full occlusion and hence prevents the user from clenching and grinding their teeth which makes the invention an effective treatment for bruxism.

By keeping the upper airway open, the upper-arch device also keeps the gastroesophageal tract closed. Hence, by keeping the upper respiratory tract open, the device provides patients with effective treatment for suffering from gastroesophageal reflux disorder (GERD).

In the preferred embodiment, the device is made of a single part of low bulk and is milled out of a bloc. The device is unobtrusive and fits easily in the user's oral cavity and can be comfortably worn during sleep.

In another embodiment, the device is made of a single part of low bulk that can be produced by CAD-CAM. The device is unobtrusive and fits easily in the user's oral cavity and can be comfortably worn during sleep.

A feature and advantage of the invention is the provision of a device that can be produced by additive manufacturing (e.g. dental CAD-CAM technology) or by milling out of a bloc and which is effective in the treatment of OSA, snoring, bruxism, temporomandibular discomfort and GERD.

A further feature of the invention is the provision of a single-arch device that gradually advances a user's lower mandible relative to the user's maxilla.

A further feature of the invention is the provision of a single-arch device that opens a user's airway and prevents it from becoming obstructed.

A further feature of the invention is the provision of a single-arch device that gradually advances a user's mandible relative to the user's maxilla and is customized to fit a user's unique mouth structure.

A further feature of the invention is the provision of a single-arch device that minimizes the number of elements and materials used and is therefore of low bulk and provides the user with a comfortable fit.

A further feature of the invention is the provision of a device that can be made of a single compound that minimizes the number of elements and materials used and is therefore less prone to the accumulation of pathogens in the interstices between assembled elements.

A further feature of the invention is the provision of a single-arch device that uses dental impressions to customize the degree of anterior protrusion for optimal placement behind the user's anterior mandibular teeth.

A further feature of the invention is the provision of a single-arch device that does not constrain and lock-in the lower mandible and allows free movement of the lower mandible relative to the maxilla, thereby reducing pressure on the TMJ and increasing comfort.

A further feature of the invention is the provision of a single-arch device that prevents clenching and bruxing by preventing full occlusal contact.

To appreciate the present contributions to the art, the above descriptions of the more important features of the invention are provided broadly to better understand the detailed descriptions that follow. Together with the accompanying figures and following descriptions, other objects and features of the invention will become apparent. The drawings are solely provided for the purposes of illustration. In no way do they constitute a definition of the limits of the invention as described in the claims below.

The second set of embodiments relates to a single-arch, gradual mandibular advancement device for the treatment of obstructive sleep apnea (OSA), snoring, bruxism, temporomandibular joint (TMJ) discomfort and gastroesophageal reflux (GERD). The medical device can be made of a single compound and gradually advances the lower mandible by sliding it along a protruding wedge element on occlusion thereby opening the upper respiratory. The mandibular advancement device fits a single-arch and is designed to treat obstructive sleep apnea (OSA) and snoring. The mandibular advancement device is of low bulk because it fits a single arch, leaving the remaining arch unconstrained. This mandibular advancement device gradually moves the lower mandible forward on occlusion by sliding the mandible along the inverted wedge element. The user's upper respiratory tract is gradually opened on occlusion as the lower mandible slides forward along the wedge element. The increase of the diameter of the upper respiratory tract facilitates the passage of air into the lungs and treats underlying conditions such as OSA and snoring. Mandibular advancement is gradual on occlusion and thus avoids the application of constant and sustained tension on the temporomandibular joint (TMJ) that is known to cause long-term complications.

FIG. 1 is a schematic, isometric view of a single-arch maxillary device 1 which is customized to fit over the maxillary teeth. Dental impressions 2 are made so that the mandibular advancement device is tailored to each patient. Extending from the central portion of the main body 3 is the protrusive wedge element 4. The protrusive wedge element allows the lower mandible 5 to gradually slide forward on occlusion and opens the upper respiratory tract.

Figure 2:
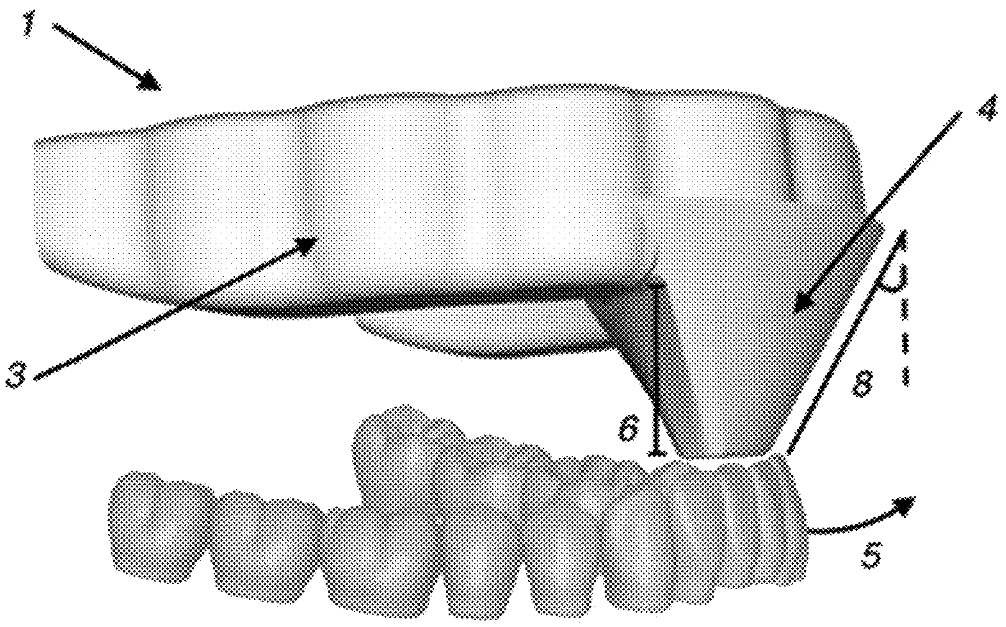
FIG. 2 is a lateral view of a single-arch maxillary device in accordance with the teachings of the present invention.

FIG. 2 is a schematic, lateral view of the single-arch maxillary device 1. The protrusive wedge element 4 descends from the anterior portion 6 of the main body 3 by about 12 mm and is angled toward the tongue at between 30-60 degrees 8 with the precise angle being determined from the ratio of the height 6 to the length of the maximal mandibular advancement. This wedge allows the lower mandible 5 to gradually slide forward on occlusion and open the upper respiratory tract.

Figure 3:
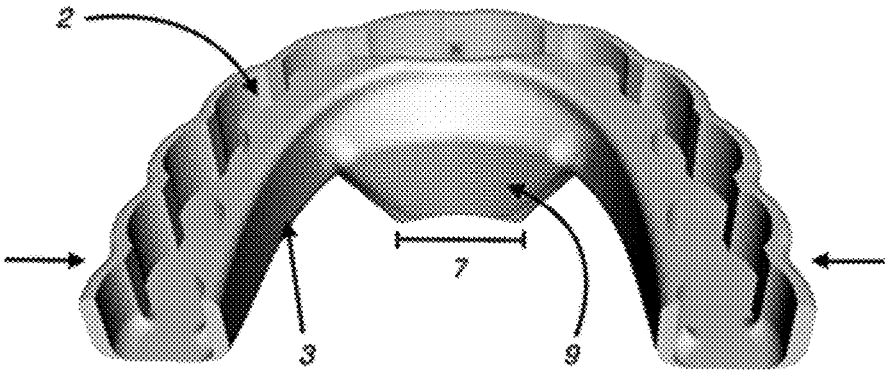
FIG. 3 is a posterior view of a single-arch maxillary device in accordance with the teachings of the present invention.

FIG. 3 is a schematic, posterior view of the single-arch maxillary device 1 showing the customized fit over the maxillary teeth. The posterior view of the protrusive wedge element 9 descending from the anterior portion of the main body has a base width 7 of about 25 mm.

Figure 4:
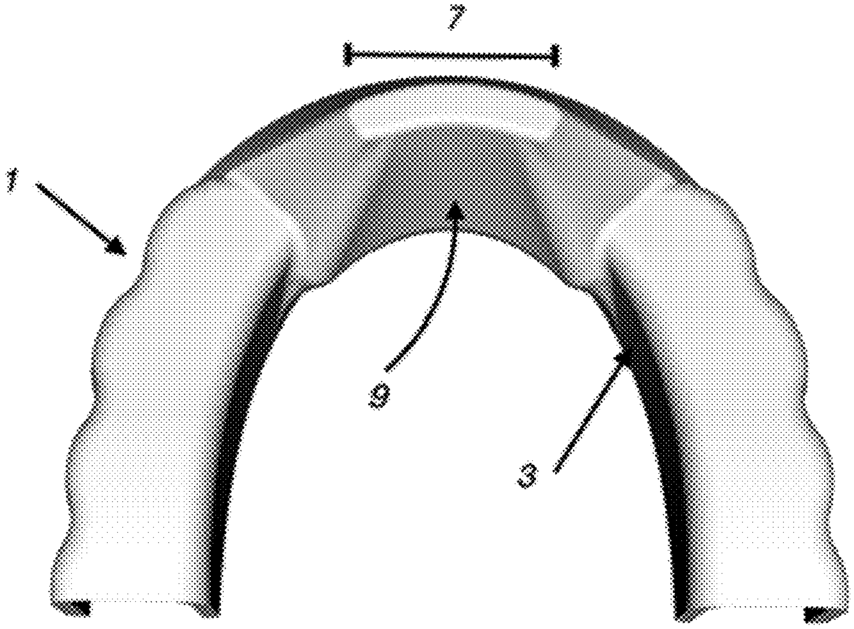
FIG. 4 is a bottom view of the single-arch maxillary device in accordance with the teachings of the present invention.

FIG. 4 is a schematic, bottom view of the single-arch maxillary device 1 showing the posterior view of the protruding wedge element 9 descending from the main body 3 and having a width 7 of about 25 mm.

Figure 5:
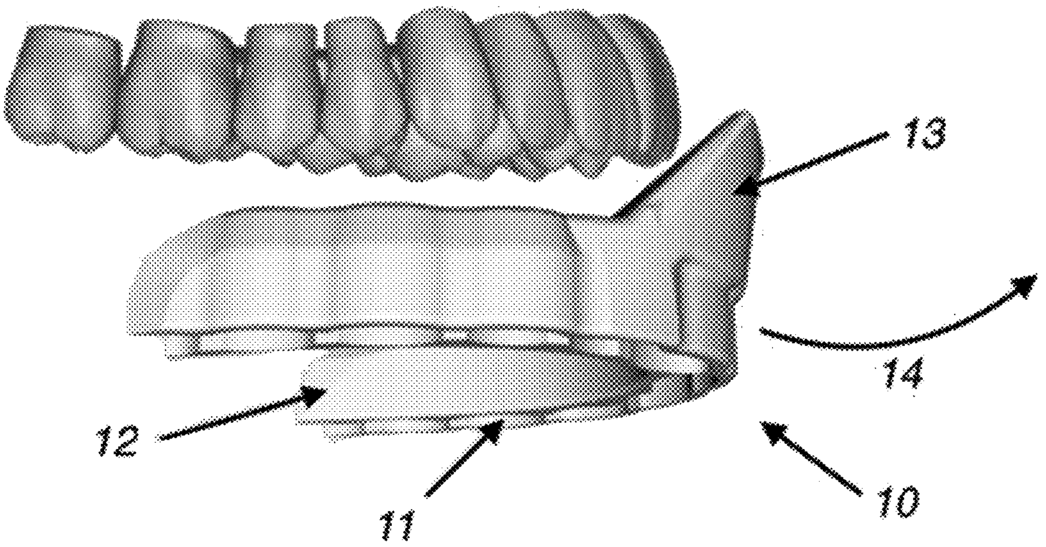
FIG. 5 is an isometric bottom view of the single-arch lower mandibular device in accordance with the teachings of the present invention.
Figure 6:
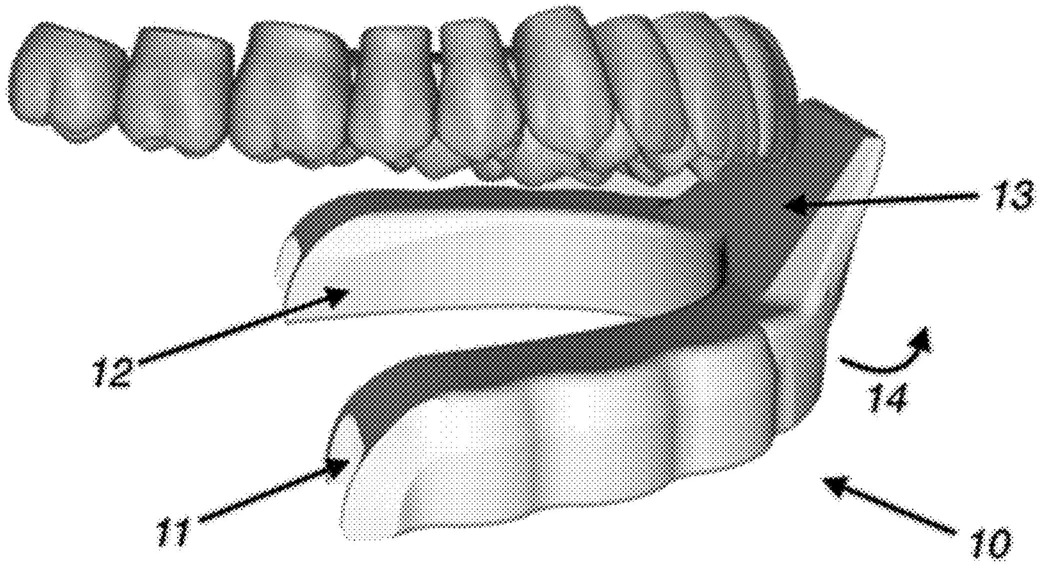
FIG. 6 is an isometric top view of the single-arch lower mandibular device in accordance with the teachings of the present invention.

FIGS. 5 and 6 are schematics, isometric views of the single-arch lower mandibular device 10 which is customized to fit over the lower mandibular teeth. Dental impressions 11 are made so that the intraoral device is customized to each patient. Extending from the central portion of the main body 12 is the protrusive wedge element 13. The protrusive wedge element 13 allows the lower mandible to slide forward 14 thereby opening the upper respiratory tract.

FIG. 7 is a schematic, posterior view of the single-arch lower mandibular device 10 showing the customized to fit over the mandibular teeth 11. The posterior view of the protrusive wedge element 13 descending from the anterior portion of the 12 main body has a base width 15 of about 25 mm.

Figure 10:
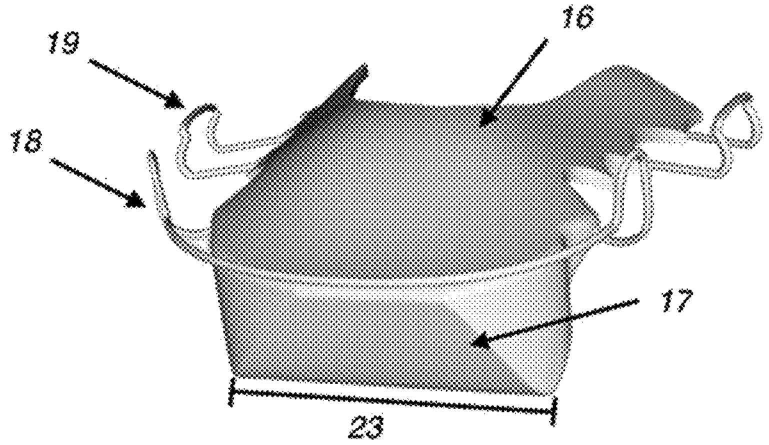
FIG. 10 is an isometric view of the single-arch palatal base plate with metal clasps in accordance with the teachings of the present invention.
Figure 11A:
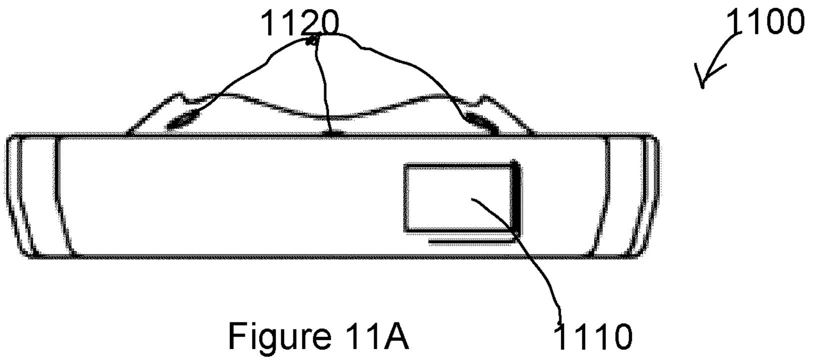
FIG. 11A and FIG. 11B, together referred to as FIG. 11, are front views of single-arch sleep monitoring devices in accordance with the teachings of the present invention.
Figure 11B:
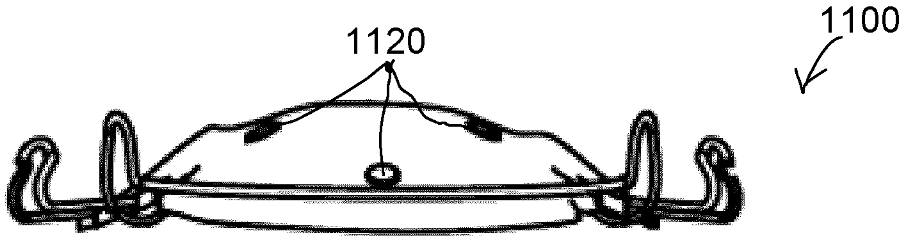
Figure 12A:
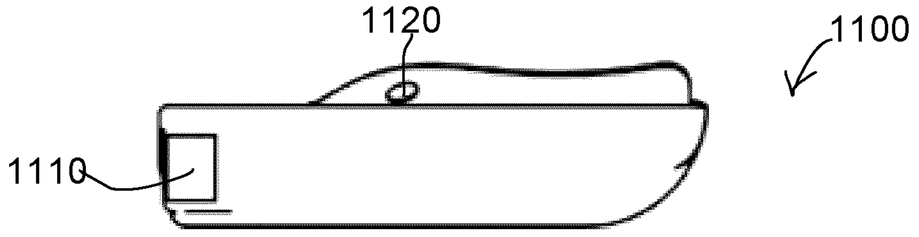
FIG. 12A and FIG. 12B, together referred to as FIG. 12, are side views of single-arch sleep monitoring devices in accordance with the teachings of the present invention.
Figure 12B:
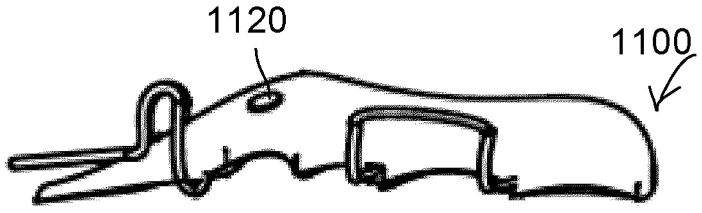
Figure 13A:
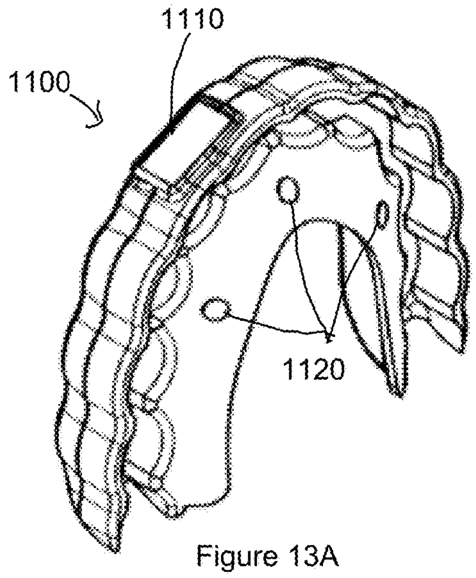
FIG. 13A and FIG. 13B, together referred to as FIG. 13, are isometric views of single-arch sleep monitoring devices in accordance with the teachings of the present invention.
Figure 13B:
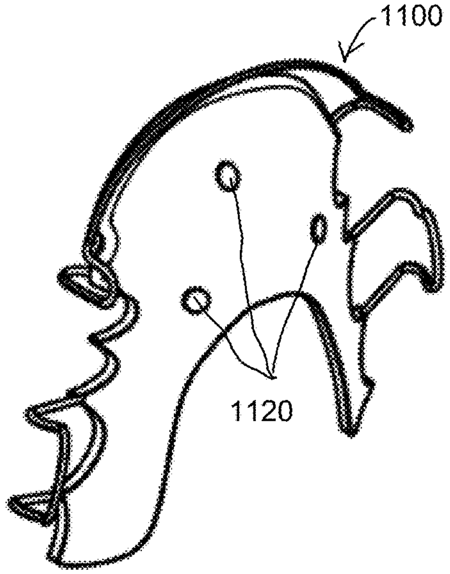
Figure 14A:
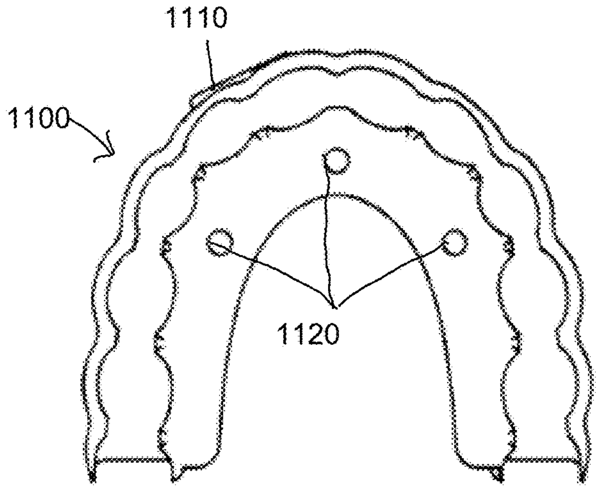
FIG. 14A and FIG. 14B, together referred to as FIG. 15, are bottom views of single-arch sleep monitoring devices in accordance with the teachings of the present invention.
Figure 14B:
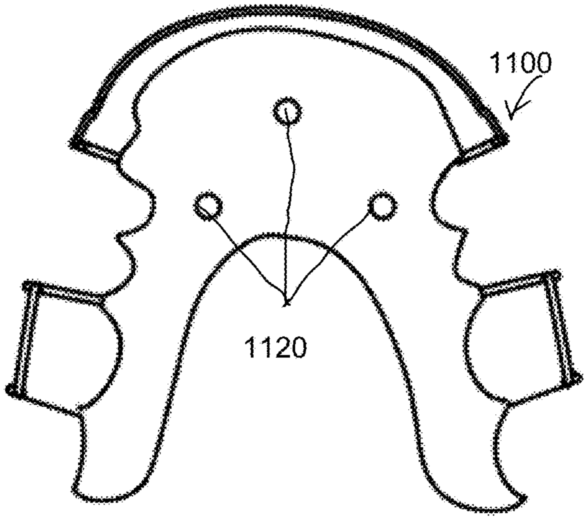
Figure 15A:
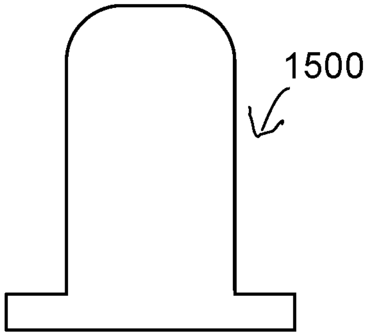
FIG. 15A, FIG. 15B, FIG. 15C and FIG. 15D, together referred to as FIG. 15, are front views of electrodes in accordance with the teachings of the present invention.
Figure 15B:
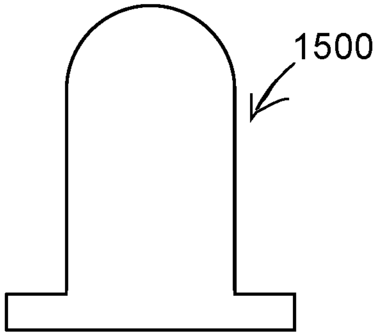
Figure 15C:
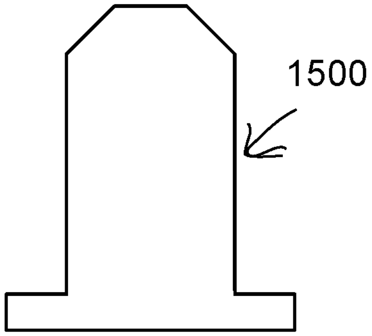
Figure 15D:
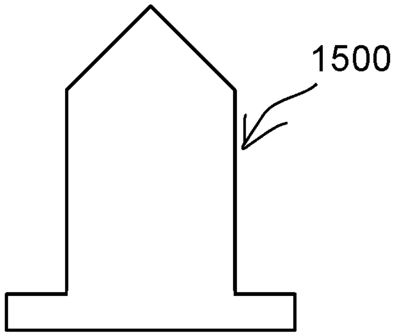

FIGS. 8 and 10 are schematics, isometric views of the single-arch palatal base plate with metal clasps 16 which is customized to fit over the palate and maxillary teeth of the user. The retention is secured by the anterior 18 and posterior 19 metal clasps. Extending from the central portion of the main body is the protrusive wedge element 17. The protrusive wedge element 17 descends from the anterior portion of the main body 21 by about 12 mm and is angled 22 toward the tongue at between 30-60 degrees with the precise angle being determined from the ratio of the height 21 to the length of the maximal mandibular advancement. The protrusive wedge element 17 allows the lower mandible 20 to slide forward thereby opening the upper respiratory tract.

Figure 9:
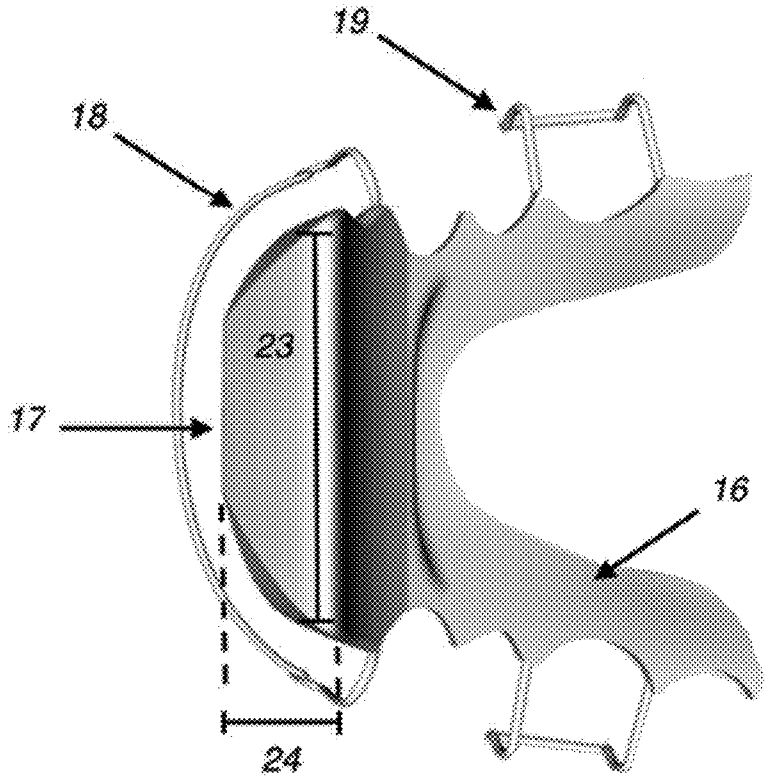
FIG. 9 is a bottom view of the single-arch palatal base plate with metal clasps in accordance with the teachings of the present invention.

FIG. 9 is a schematic, bottom view of the single-arch palatal base plate with metal clasps 16 showing the posterior view of the protrusive wedge element 17 descending from the main body and having a base width 23 of about 25 mm and extension length 24 of about 12 mm. The angle of the wedge is determined by the ratio of the height 21 to the extension length 24.

The third set of embodiments relates to a dynamic mandibular adjustment device comprising a mechanical actuator that uses measurement device(s) and/or sensors, of a measurement device module, to determine the user's breathing status in real-time and, accordingly, adjust the position of the lower mandible. The medical device comprises a pair of upper and lower jaws causing binding of upper and lower teeth together and forcing the lower mandible forward when required. The mechanical actuator causes a bloc element to dynamically change the amount of adjustment of the lower mandible and settle the position of the lower mandible in the location that improves the user's breathing. The bloc element may have a flat surface (i.e. not inclined wedge) that binds to lower teeth in a way that keeps both upper and lower jaws locked in. The mandibular adjustment can be obtained by advancement or retraction of the mandible. The mandibular adjustment is effected while taking into account the range of acceptable adjustment distance. The advancement distance ranges, on average, between 8 mm and 12 mm. The maximal acceptable adjustment distance can be determined clinically using impressions. Alternatively, the acceptable adjustment distance range may be determined considering the extra tension occurring in the masseter muscle due to mandibular adjustment. The extra tension in the masseter muscle could be determined, in vivo, by measuring the pressure exerted on the device by the user's teeth.

Upon determination of the user's breathing status by the measurement device(s) and/or sensors, the mechanical actuator adjusts the mandibular advancement distance. Thus, during periods when the user wears the device and breathes well, no adjustment distance or a basic adjustment distance is effected. However, when the user's breathing is more strained and a breathing issue is detected, the actuator advances the lower mandible accordingly. Examples of breathing issues include obstructive sleep apnea (OSA) and snoring.

Figure 16:
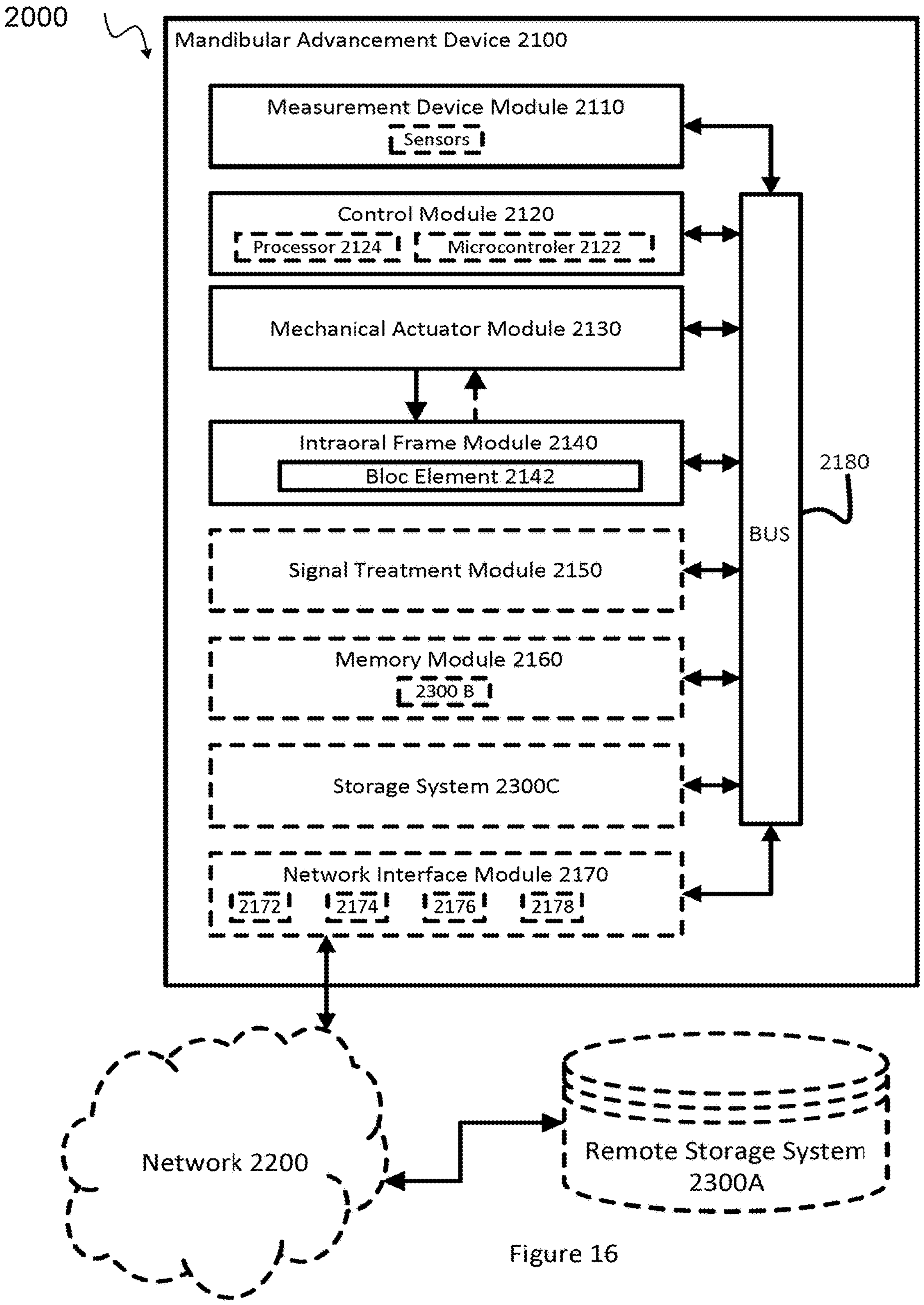
FIG. 16 is a modular representation of a dynamic mandibular adjustment device in accordance with the teachings of the present invention.

FIG. 16 shows a logical modular representation 2000 of a dynamic mandibular adjustment device 2100 performing a mandibular adjustment, in accordance with the teachings of the present invention.

In the depicted example of FIG. 16, the dynamic mandibular adjustment device 2100 comprises a control module 2120 and optionally a memory module 2160 and a network interface module 2170. The control module 2120 may represent a single processor 2124 with one or more processor cores or an array of processors, each comprising one or more processor cores. The memory module 2160 may comprise various types of memory (different standardized or kinds of Random Access Memory (RAM) modules, memory cards, Read-Only Memory (ROM) modules, programmable ROM, etc.). The network interface module 2170 represents at least one physical interface that can be used to communicate with other network nodes. The network interface module 2170 may be made visible to the other modules of the dynamic mandibular adjustment device 2100 through one or more logical interfaces. The actual stacks of protocols used by the physical network interface(s) and/or logical network interface(s) 2172, 2174, 2176, 2178 of the network interface module 2170 do not affect the teachings of the present invention. The variants of control module 2120, memory module 2160 and network interface module 2170 usable in the context of the present invention will be readily apparent to persons skilled in the art.

A bus 2180 is depicted as an example of means for exchanging data between the different modules of the dynamic mandibular adjustment device 2100. The present invention is not affected by the way the different modules exchange information between them. For instance, the memory module 2160 and the control module 2120 could be connected by a parallel bus, but could also be connected by a serial connection or involve an intermediate module (not shown) without affecting the teachings of the present invention.

Likewise, even though explicit mentions of the memory module 2160 and/or the control module 2120 are not made throughout the description of the various embodiments, persons skilled in the art will readily recognize that such modules are used in conjunction with other modules of the dynamic mandibular adjustment device 2100 to perform routine as well as innovative steps related to the present invention.

The dynamic mandibular adjustment device 2100 may comprise a storage system 2300 for storing and accessing long-term data and may further log dynamic data while the device is being used. FIG. 16 shows examples of the storage system 2300 as a distinct database system 2300A, a distinct module 2300C of the dynamic mandibular adjustment device 2100 or a sub-module 2300B of the memory module 2160 of the dynamic mandibular adjustment device 2100. The storage system 2300 may be distributed over different systems A, B, C. The storage system 2300 may comprise one or more logical or physical as well as local or remote hard disk drive (HDD) (or an array thereof). The storage system 2300 may further comprise a local or remote database made accessible to the dynamic mandibular adjustment device 2100 by a standardized or proprietary interface or via the network interface module 2170. The variants of storage system 2300 usable in the context of the present invention will be readily apparent to persons skilled in the art.

In the depicted example of FIG. 16, the dynamic mandibular adjustment device 2100 shows optional remote storage system 2300A which may communicate through the network 2200 with the dynamic mandibular adjustment device 2100. The storage module 2300, (e.g., a networked data storage system) accessible to all modules of the dynamic mandibular adjustment device 2100 involved in the mandibular adjustment via the network interface module 2170 through a network 2200, may be used to store data related to the user's respiratory status. The network interface module 2170 may also be used for enabling distribution of the control module 2120 into distinct physical enclosures.

The measurement device(s) and/or sensors provided by the measurement device module 2110 would typically vary in relation to the user's physical and respiratory status to be measured or monitored. In the example of the dynamic mandibular adjustment device 2100, the measurement device module 2110 may comprise a PPG probe, ECG probe, EEG probe, pressure sensor, temperature sensor, sound intensity sensor, accelerometer and/or gyroscope, a blood chemical sensor, etc. similar or identical to the same sensors and measurement devices discussed with reference to the first set of embodiments. While the present invention is applicable to mandibular adjustment, skilled persons will readily recognize and be able to apply its teachings to other types of monitoring systems.

The signal treatment module 2150 may proceed to a data cleaning of the data collected by the different measurement devices. For instance, the data cleaning may be used to remove noise that can be attributed to external sources (e.g., cell phone noises, body movements, alarms . . . ) or to remove data related to sleep movements such as Hypnic jerks, Propriospinal myoclonus, Epileptic myoclonus. . . .

The signal treatment module 2150 performs tasks such as filtering and eliminating a signal of unwanted components, detecting and extracting a useful component of a signal and/or the background noise superimposed on it and isolating the components and desired characteristics of a signal. Examples of data treatment include using data from the accelerometer to condition the PPG data that is sensitive to motion.

The mechanical actuator module 2130 comprises a mechanical actuator (not shown) providing one or more mechanical assemblies for physically moving the bloc element 2142 of the intraoral frame module 2140. The mechanical actuator may receive one or more sets of instructions (e.g., from the control module 2120) for causing one or more of the bloc elements 2142 to move in accordance with the received instructions. The mechanical actuator may also alternatively or in addition be used for providing feedback. For example, the feedback may be related to the pressure exerted on the mandible by the bloc element 2142.

The bloc element 2142, in some embodiments, may be provided with a fail-safe mechanism to improve the safety of the user and minimize the damage that may be caused by a high pressure on the mandible. For instance, the bloc element 2142 might be configured to break off or interrupt the mandibular adjustment when a pressure exceeding a predetermined threshold value is applied thereto.

The feedback provided by the mechanical actuator may be related to the position of the mandible after adjustment. Among others, inductive sensors and Hall effect sensors can be used to determine the position of the mandible after the mandibular adjustment. The inductive sensors are used to detect objects able to interact with a magnetic field. A metallic element could be integrated to the dynamic mandibular adjustment device allowing the inductive sensor to detect the position of the device. The Hall effect sensors measure the magnitude of a magnetic field and can be used to determine the position of the dynamic mandibular adjustment device. Once the position of the dynamic mandibular adjustment device is known, the position of the mandible and the effective mandibular adjustment can be computed.

The different functions performed by the dynamic mandibular adjustment device 2100 can be distributed over multiple nodes. For example, the dynamic mandibular adjustment device may comprise one or more remote parts containing one or more modules such as: storage system 2300A and signal treatment module 2150. More specifically, in certain embodiments, the control module 2120 and/or the signal treatment module 2150 may access the mechanical actuator module 2130 and/or the measurement device module 2110 through the network interface module 2170. The control module 2120 and/or the signal treatment module 2150 may therefore be remote from the dynamic mandibular adjustment device and be located in close proximity thereto (e.g., short range radio communication) or remotely (e.g., functions provided in the local network and/or remotely such as through a cloud processing service).

Various network links may be implicitly or explicitly used in the context of the present invention. While a link may be depicted as a wireless link, it could also be embodied as a wired link using a coaxial cable, an optical fiber, a category 5 cable, and the like. A wired or wireless access point (not shown) may be present on the link between. Likewise, any number of routers (not shown) may be present and part of the link, which may further pass through the Internet.

The dynamic mandibular adjustment device also comprises or may be connected to a sealed a power source. The power source may be mounted or integrated within the mandibular advancement device. In some embodiments, the power source is rechargeable (wirelessly rechargeable battery; gyroscope-based rechargeable battery; solar-power rechargeable battery; etc.), but it may also be a single charge battery. In some embodiments, the dynamic mandibular adjustment device comprises a charging port (e.g. on the BUS 2180 or elsewhere).

The one or more measurement devices may comprise a photoplethysmogram (PPG) sensor integrated in the measurement device module 2110 or mounted on or integrated within the dynamic mandibular adjustment device 2100 facing the palate of the wearer, such that the PPG sensor is in contact or close proximity with one or more blood vessels of the wearer. The PPG sensor can be used to measure blood O2 levels, heart rate and may further provide basic data to extract respiratory rate and blood pressure. The data produced by a plurality of photoplethysmogram (PPG) sensors and a Pulse Transit Time (PTT) may be combined to compute the blood pressure in real time. In some embodiments, necessary electrical connectivity between the PPG sensor and the control module 2120 are added during the manufacturing step (e.g., as wires or as 3D printable conductive material). In other embodiments, the PPG sensor is in wireless communication with control module 2120 (e.g., Bluetooth, proprietary protocol, etc.).

The one or more measurement devices may comprise a pressure transducer or a pressure switch integrated in the measurement device module 2110 or mounted on or integrated within (a non-airtight compartment of) the dynamic mandibular adjustment device 2100. The pressure transducer or a pressure switch can be used to measure variations in intraoral air pressure to indicate respiratory frequency and/or occlusal pressure, which could be useful to monitor bruxism. In some embodiments, necessary electrical connectivity between the pressure transducer or a pressure switch and the control module 2120 are added during the manufacturing step (e.g., as wires or as 3D printable conductive material). In other embodiments, the pressure transducer or a pressure switch is in wireless communication with the control module 2120 (e.g., Bluetooth, proprietary protocol, etc.).

The one or more measurement devices may comprise a temperature sensor integrated in the measurement device module 2110 or mounted on or integrated within the dynamic mandibular adjustment device. The temperature sensor can be used to measure variations in intraoral temperature. In some embodiments, necessary electrical connectivity between the temperature sensor and the control module 2120 are added during the manufacturing step (e.g., as wires or as 3D printable conductive material). In other embodiments, the temperature sensor is in wireless communication with the control module 2120 (e.g., Bluetooth, proprietary protocol, etc.).

The one or more measurement devices may comprise EEG (Electroencephalography) probes, such as the examples depicted on FIG. 15, may be mounted on or integrated within (e.g., at the openings 1120) the dynamic mandibular adjustment device. The EEG probes can be used to measure electroencephalography data. In some embodiments, necessary electrical connectivity between the EEG probes and the control module 2120 are added during the manufacturing step (e.g., as wires or as 3D printable conductive material). In other embodiments, the EEG probes is in wireless communication with the control module 2120 (e.g., Bluetooth, proprietary protocol, etc.).

The one or more measurement devices may comprise one or more accelerometer and/or gyroscope sensors integrated in the measurement device module 2110 or mounted on or integrated within the mandibular advancement device. The one or more accelerometer and/or gyroscope sensors can be used to measure head movements and body vibrations of the wearer. The head movements and body vibrations can be used as indicators of the wearer's sleep state (e.g. awake, REM sleep, light sleep, deep sleep). Similarly, the head movements and body vibrations of the wearer may then be used to extrapolate restless leg syndrome and other movement-based sleep disorders. The one or more accelerometer and/or gyroscope sensors may also be used to provide the necessary data to clean out the PPG signal. The one or more accelerometer and/or gyroscope sensors may also be used to detect high frequency jerk-lie movements that signal restless limbs syndrome or other myoclonic (involuntary) muscle activity during sleep. In some embodiments, necessary electrical connectivity between the one or more accelerometer and/or gyroscope sensors and the control module 2120 are added during the manufacturing step (e.g., as wires or as 3D printable conductive material). In other embodiments, the one or more accelerometer and/or gyroscope sensors is in wireless communication with the control module 2120 (e.g., Bluetooth, proprietary protocol, etc.).

The one or more measurement devices may comprise electrocardiogram (EKG or ECG) probes, such as the examples depicted on FIG. 15, may be mounted on or integrated within (e.g., at the openings 1120) the dynamic mandibular adjustment device. The ECG probes can be used to measure heart performance data. In some embodiments, necessary electrical connectivity between the ECG probes and the control module 2120 are added during the manufacturing step (e.g., as wires or as 3D printable conductive material). In other embodiments, the ECG probes is in wireless communication with the control module 2120 (e.g., Bluetooth, proprietary protocol, etc.). The ECG probes may, for instance, take the form of small microelectromechanical systems (MEMS).

The one or more measurement devices may comprise a sound sensor integrated in the measurement device module 2110 or mounted on or integrated within the mandibular advancement device. The sound sensor can be used to measure variations in sound (e.g., intensity of snoring noise and breathing effort). In some embodiments, necessary electrical connectivity between the sound sensor and the control module 2120 are added during the manufacturing step (e.g., as wires or as 3D printable conductive material). In other embodiments, the sound sensor is in wireless communication with the control module 2120 (e.g., Bluetooth, proprietary protocol, etc.). Among others, the sound sensor is a directional microphone or a dB meter. The dB meter provides a dB measure related to intraoral noise that may be used to determine the extent of dynamic advancement in the actuator.

The one or measurement devices may comprise a blood-chemical sensor integrated in the measurement device module 2110 or mounted on or integrated within the mandibular advancement device. The blood-chemical sensor can be used to measure variations in blood levels of one or more chemicals present in the wearer's blood. In some embodiments, necessary electrical connectivity between the blood-chemical sensor and the control module 2120 are added during the manufacturing step (e.g., as wires or as 3D printable conductive material). In other embodiments, the blood-chemical sensor is in wireless communication with the control module 2120 (e.g., Bluetooth, proprietary protocol, etc.). Examples of blood chemical that may be measured include cortisol and glucose. Other biomarkers that fluctuate during sleep may be measured and can indicate important information with respect to sleep disorders.

In accordance with the third set of embodiments, one or more measurement devices (as discussed with reference to the first set of embodiments) may be integrated into a mandibular adjustment device. The mandibular adjustment device is designed to treat obstructive sleep apnea (OSA), snoring, bruxism, temporomandibular discomfort and/or gastroesophageal reflux (GERD). Example of sensors and measurement devices include PPG probe, ECG probe, EEG probe, pressure sensor, temperature sensor, sound intensity sensor, accelerometer and/or gyroscope, a blood chemical sensor, etc. similar or identical to the same sensors and measurement devices discussed with reference to the first set of embodiments.

The mechanical actuator is adapted to cause the bloc element 2142 to modify, in real time, the adjustment distance between the minimum distance and the maximum upon modification of the user's respiration. The bloc element pushes the lower mandible allowing it to slide forward. The pressure required to push the mandible forward can be obtained by translation, rotation or deformation of the bloc element 2142.

The control module can comprise a microcontroller 2122 to monitor the adjustment distance of the mandible. The microcontroller 2122 can be integrated in the control module 2120 or mounted on or integrated within the dynamic mandibular adjustment device 2100. Optionally, the microcontroller 2122 may be configured to allow a remote control of the mechanical actuator 2130. In some embodiments, necessary electrical connectivity between the microcontroller and the control module 2120 are added during the manufacturing step (e.g., as wires or as 3D printable conductive material). In other embodiments, the microcontroller 2122 is in wireless communication with the control module 2120 (e.g., Bluetooth, proprietary protocol, etc.). In other embodiments, the microcontroller can be integrated directly into the mechanical actuator module 2130.

The adjustment distance can be obtained by converting energy into a mechanical modification of the bloc element 2142 using one or more approaches such as: piezoelectric effect, electrostatic effect, electromagnetic effect, hydraulic effect and shape-memory alloy properties. Skilled persons will recognize that other means may be used without affecting the teachings of the invention.

The one or more distance adjustment approaches can be based on a piezoelectric element. The piezoelectric element can be used to achieve the adjustment distance as the dimensions of the piezoelectric element are modified by the application of a voltage on the piezoelectric element. The piezoelectric element can provide adjustment of range of a few millimeters (5-7 mm). Because the device is to be used in vivo, the piezoelectric effect is more likely to be used if the high voltage it needs to operate can be reduced and/or if security aspects related to the high voltage can otherwise be addressed.

The one or more distance adjustment approaches can take advantage of the electromagnetic effect in which the principle of transformation is based on force interaction in a magnetic field. The electromagnetic effect is more likely to be used if the limits imposed by the high current it needs to be generated are exceeded.

The one or more distance adjustment approaches can be achieved by a hydraulic actuator comprising a hollow cylinder having a piston inserted in it. Upon the application of an unbalanced pressure to the piston, as the liquid is incompressible, the hollow cylinder generates a force able to move external objects.

The one or more distance adjustment approaches can be achieved by shape memory alloys that are known to be able to retrieve an initial shape, previously stored, when heated due to thermal expansion.

Microelectromechanical systems (MEMS) technology is used for constructing a micro actuator. The Microelectrochemical systems (MEMS) technology combines electrical and mechanical components together to produce a system of miniature dimensions allowing to sense and control the environment and thus produce a micro actuator with high level of portability and lightness allowing a comfortable wearing of the device.

In the context of the depicted embodiments, runtime execution, real-time execution or real-time priority processing execution corresponds to operations executed while measuring the breathing status. An operation performed at runtime, in real-time or using real-time priority processing thus typically needs to meet certain performance constraints that may be expressed, for instance, in terms of maximum time and/or maximum number of processing cycles. Skilled persons will readily recognize that real-time processing may not actually be achievable in absolutely all circumstances. The real-time priority processing required for the purpose of the disclosed embodiments relates to perceived responsiveness by the user of the dynamic mandibular adjustment device, and does not require absolute real-time processing of all dynamic events, even if the user was to perceive a certain level of deterioration of quality of responsiveness that would still be considered effective.

The third set of embodiments relates to a dynamic intraoral, mandibular adjustment device for the treatment of obstructive sleep apnea (OSA), snoring, bruxism, temporomandibular joint (TMJ) discomfort and gastroesophageal reflux (GERD). The medical device can be made of a single compound and dynamically advances the lower mandible, in real-time, by sliding it along a bloc element thereby opening the upper respiratory. The dynamic mandibular adjustment device is designed to treat obstructive sleep apnea (OSA), snoring, bruxism, temporomandibular discomfort and gastroesophageal reflux (GERD). This intraoral mandibular adjustment device dynamically moves the lower mandible forward by horizontally sliding the mandible along the bloc element. The user's upper respiratory tract is gradually opened as the lower mandible slides forward along the bloc element. The increase of the diameter of the upper respiratory tract facilitates the passage of air into the lungs and treats underlying conditions such as OSA, snoring, bruxism, temporomandibular discomfort and GERD. Mandibular advancement is dynamic and thus avoids the application of constant and sustained tension on the temporomandibular joint (TMJ) that is known to cause long-term complications.

In certain embodiments of the first, second and third sets of embodiments, a processing agent (not shown) may be provided for additional ex-situ treatment of data from the control module 2120, the signal treatment module 2150 and/or the measurement device module 2110. The processing agent may be remote from the dynamic mandibular adjustment device 2100 and form a remote part (not shown).

Depending on the choices made in its implementation, the remote part may provide at least one exemplary advantage such as having devices that can run on low-cost hardware while providing a possible statistical-gathering system with a varying number of wearers (e.g., as part of a research program) and/or providing adjustable processing power by utilizing distributed processing/virtualized hardware (e.g., cloud-based or cluster-based) for running the processing agent. The communication between the dynamic mandibular adjustment device 2100 and the processing agent would occur through the network interface module 2170 directly, e.g., via a local network or a Wide Area Network (WAN) interface, or indirectly, e.g., through an optional network interface 2172. The WAN interface could be based on Ethernet or other wireline protocol or could be a wireless interface (e.g., 3G, WiMax, 4G/LTE, 5G, cellular network, etc.). Skilled persons will readily understand that the connection is a logical connection and that different network nodes (e.g., routers, switches, etc.) may be present thereon. In one embodiment, the measurement device module 2110 of the dynamic mandibular adjustment device 2100 is connectable to a network interface of the remote part (e.g., through the network interface module 2170) to form a local connection. In order for the local connection to occur therebetween, the remote part should be at least temporarily co-located with the dynamic mandibular adjustment device 2100. The dynamic mandibular adjustment device 2100 may then exchange data (e.g., send and receive instructions) with the remote part. The remote part may be provided as a smartphone, a smart tablet, a portable or fixed computer or the likes. In addition, the remote part may further allow the dynamic mandibular adjustment device 2100 to communicate with the processing agent therethrough. The local interface may further be a local wired interface (USB, FireWire®, Ethernet, etc.) or a local wireless interface (Near Filed Communication (NFC), Bluetooth®, Wi-Fi™ etc.)

The control module 2120 is depicted as the exemplary element that performs computing functions of the device 2100 (e.g., managing a buffer for the measurements, providing a basic instruction set, interface with the measurement device module 2110, etc.). The control module 2120 may represent a single processor 2124 with one or more processor cores or an array of processors, each comprising one or more processor cores and a memory module, which may comprise various types of memory (different standardized or kinds of Random Access Memory (RAM) modules, memory cards, Read-Only Memory (ROM) modules, programmable ROM, etc.). The control module 2120 may further comprise a network interface module comprising at least one physical interface that can be used to communicate with other network nodes. The network interface module may be made visible to the other modules of the control module 2120 through one or more logical interfaces. The actual stacks of protocols used by the physical network interface(s) and/or logical network interface(s) of the network interface module do not affect any of the exemplary embodiments described herein. The variants of the control module 2120 comprising the memory module and the network interface module usable in the context of the exemplary embodiments will be readily apparent to persons skilled in the art. Likewise, even though explicit mention of the control module 2120 is not made throughout the description of the various examples, persons skilled in the art will readily recognize that such modules are used in conjunction with other modules of the dynamic mandibular adjustment device 2100 to perform routine as well as innovative steps related to the present invention.

Figure 17:
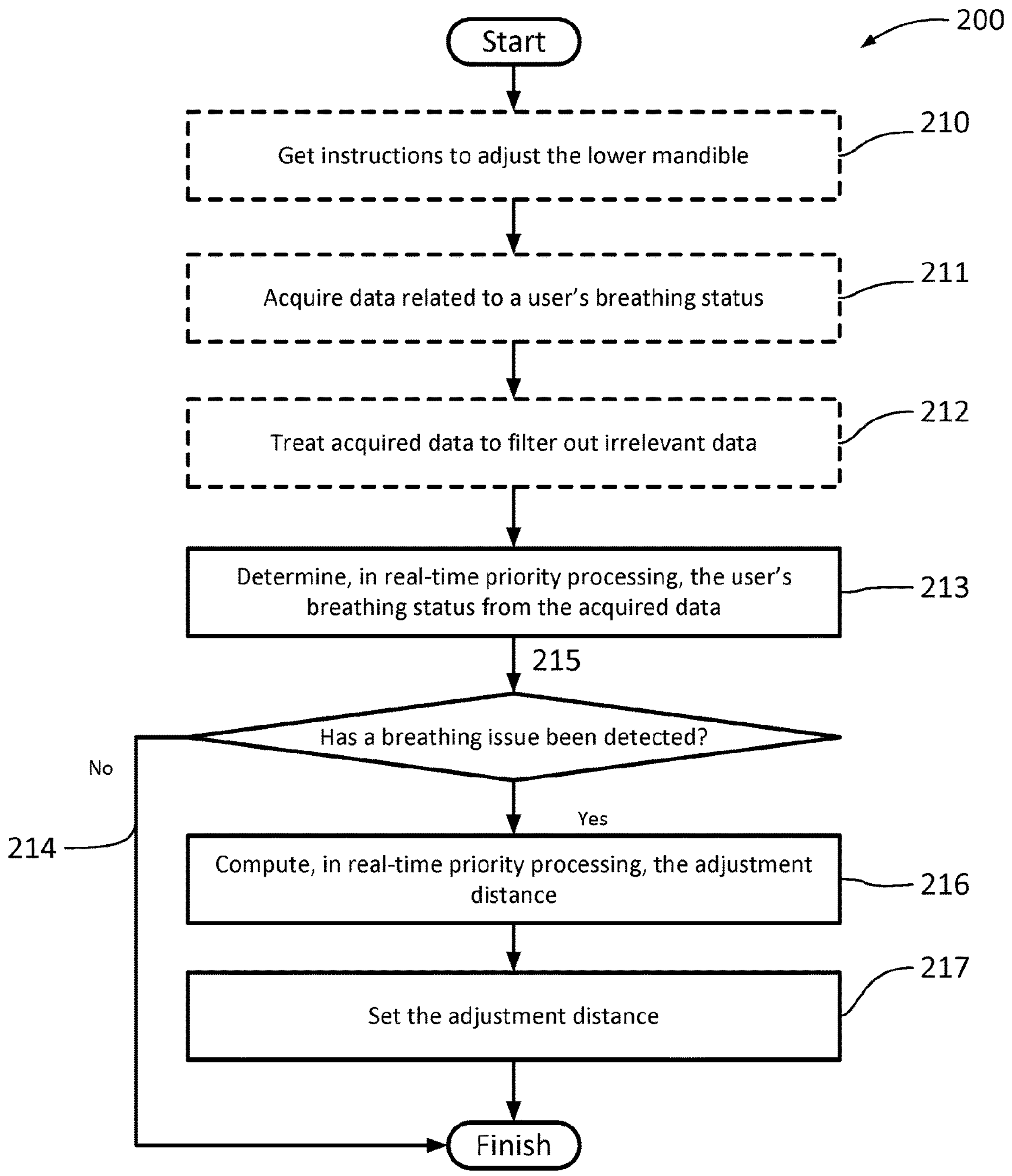
FIG. 17 is a flow chart of a first exemplary method in accordance with the teachings of the present invention.

FIG. 17 illustrates a method 200 for repositioning a user's mandible in accordance with one or more implementations. The operations of method 200 presented below are intended to be illustrative. In some implementations, the method 200 may be accomplished with one or more additional operations not described, and/or without one or more of the operations discussed. Additionally, the order in which the operations of the method 200 are illustrated in FIG. 17 and described below is not intended to be limiting.

The method 200 is for repositioning a user's mandible. The method 200 may include acquiring 211 data related to a user's breathing status and treating 212 the acquired data to filter out irrelevant data. The method 200 also includes determining 213 in real-time priority processing the user's breathing status. Additionally, the method 200 includes computing 216 in real-time priority processing an adjustment distance and setting 217 the adjustment distance causing a bloc element to push forward the mandible in cases where a breathing issue is detected 215. The adjustment may be effected to return the mandible to a resting position if no breathing issue is detected. The method 200 may be terminated 214 if no advancement is needed. The method 200 may include storing the acquired data and/or distributing the acquired data.

Figure 18:
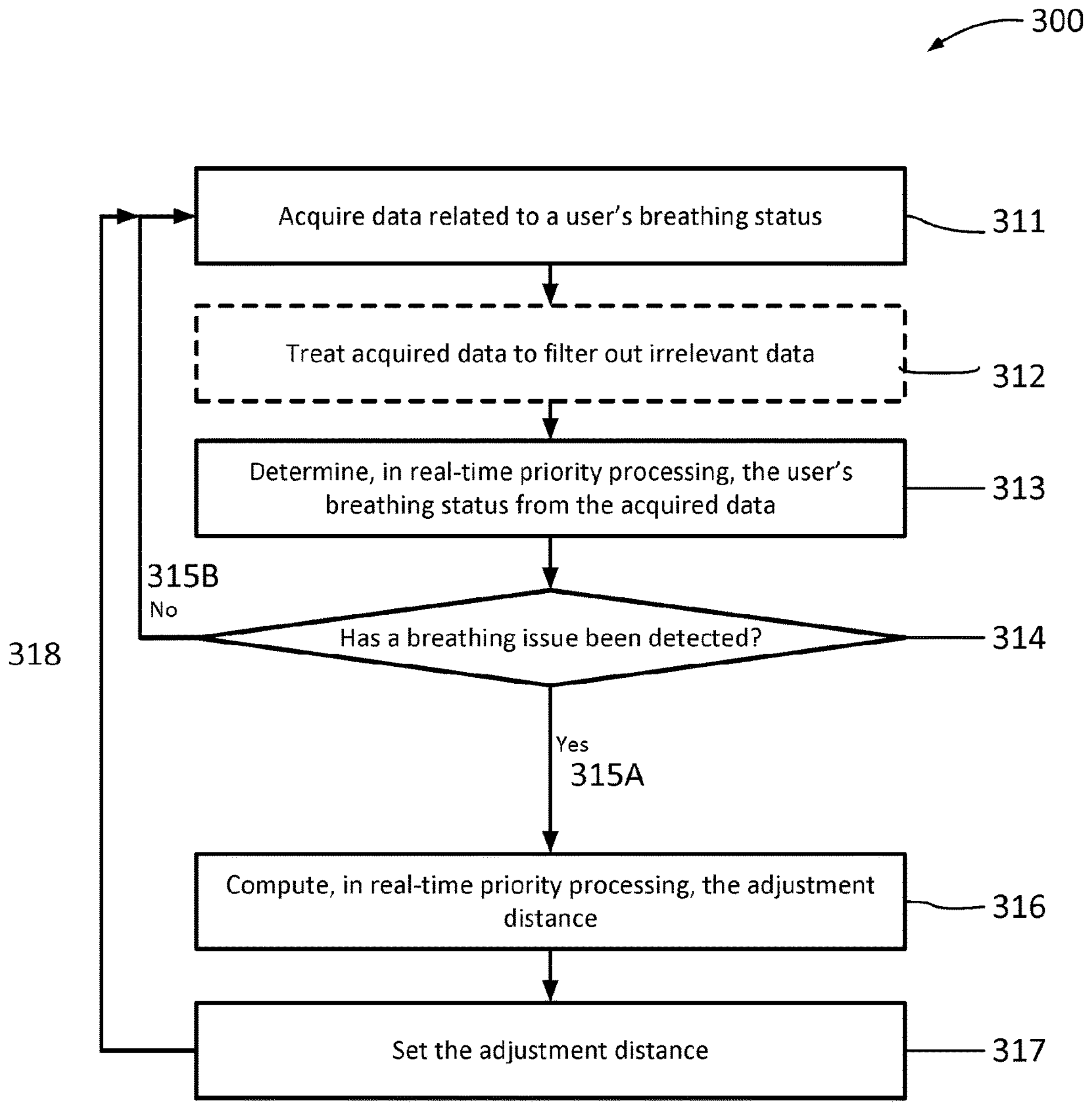
FIG. 18 is a flow chart of a second exemplary method in accordance with the teachings of the present invention.
Figure 19:
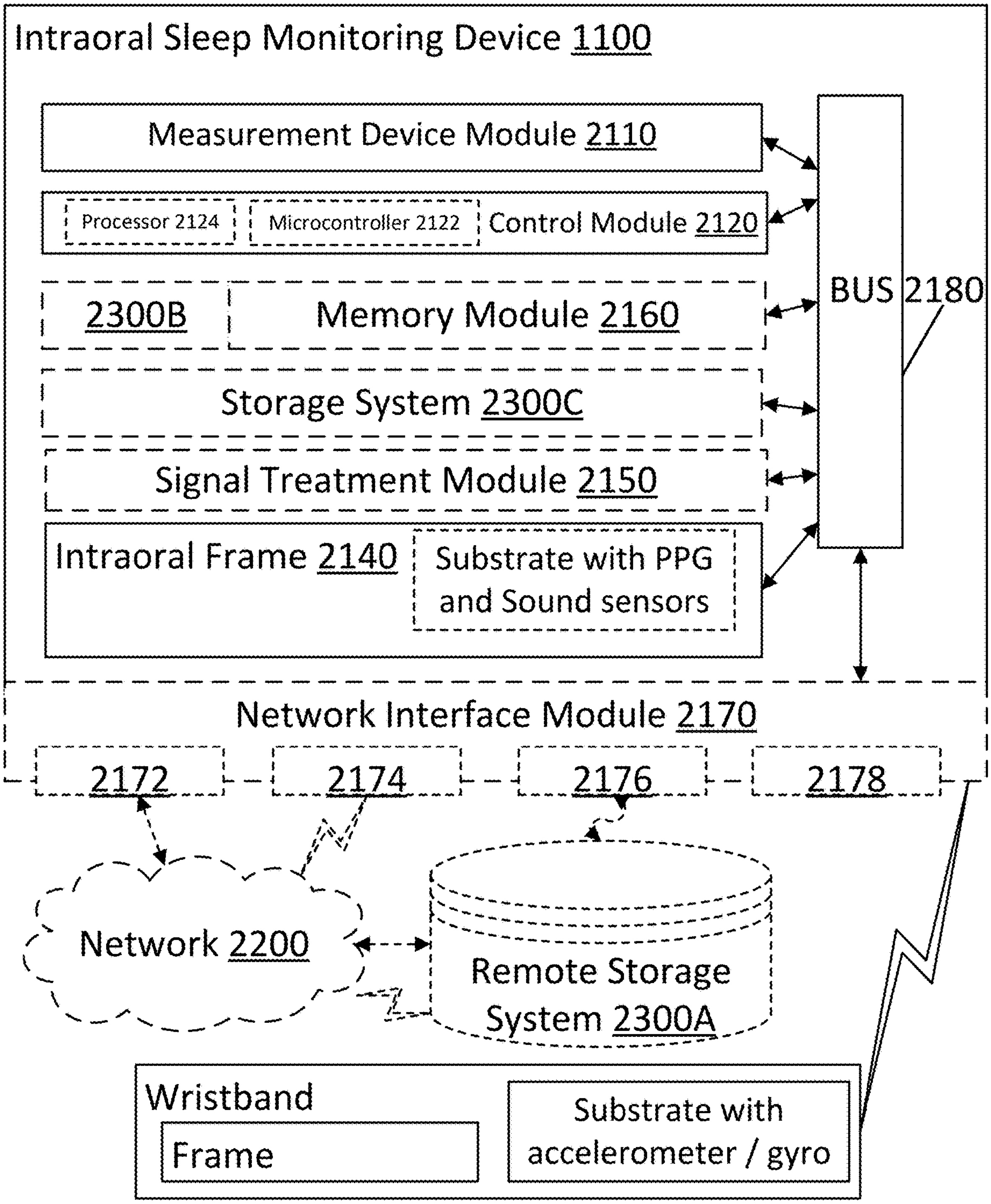
FIG. 19 is a modular representation of an intraoral sleep monitoring device system in accordance with the teachings of the present invention.

FIG. 18 illustrates a method 300 for repositioning a user's mandible in accordance with one or more implementations.

The method 300 is for repositioning a user's mandible. The method 300 may include acquiring 311 data related to a user's breathing status and treating 312 the acquired data to filter out irrelevant data. The method 300 also includes determining 313 in real-time priority processing the user's breathing status. Additionally, the method 300 includes computing 316 in real-time priority processing an adjustment distance and setting 317 the adjustment distance causing a bloc element to push forward the mandible in cases where a breathing issue is detected 315A. The adjustment may be effected to return the mandible to a resting position if no breathing issue is detected. If no breathing issue is detected 315B or the adjustment distance is set 318, the steps of the method are repeated. The method 300 may include storing the acquired data and/or distributing the acquired data. The steps of the method 300 are repeated as long as the mandibular adjustment device is worn by the user.

In some implementations of the method, acquiring data related to a user's breathing status may be performed using a plurality of measurement devices such as: PPG probe, ECG, EEG probe, pressure sensor, temperature sensor, sound sensor, accelerometer and/or gyroscope, etc. Furthermore, an intraoral sound sensor may be used to detect the user's intraoral noise. A control module such as the control module 2120 depicted with reference to FIG. 16 may be used to compute, in real-time priority processing, the adjustment distance. Additionally, setting the adjustment distance may be performed by a mechanical actuator such as the mechanical actuator module 2130 depicted with reference to FIG. 16. The mechanical actuator may take into account a feedback related to the pressure exerted on the mandible to minimize the damage that may be caused by a high pressure on the mandible. Storing the acquired data may be performed by a storage system, such as the storage system 2300 of FIG. 16, for the long-term data and by a memory module, such as the memory module 2160 of FIG. 16, for the short-term data.

In some embodiments, the method may be executed at an established frequency. In another embodiment, the method can support on demand adjustment 210. One disadvantage of this feature is the potential discomfort it would cause.

In accordance with a fourth set of embodiments, a method (not shown) for treating data collected by one or more measurement devices is provided. The method for treating the data may be used to remove noise that can be attributed to external sources (e.g., cell phone noises, body movements, alarms, quality of input equipment, . . . ) or to remove data related to sleep movements such as hypnic jerks, propriospinal myoclonus, epileptic myoclonus. The collected data are treated by a signal treatment module (not shown) similar to and adapted, mutatis mutandis, from the signal treatment module 2150 depicted in the context of the previously described dynamic mandibular adjustment device 2100. For greater certainty, it can be said that the signal treatment module performs tasks such as filtering and eliminating a signal of unwanted components, detecting and extracting a useful component of a signal and/or the background noise superimposed on it and isolating the components and desired characteristics of a signal. The data treatment module may combine data from two or more measurement devices to isolate the characteristics of relevant signals to help medical specialists to interpret the data. Examples of combining data from a plurality of measurement devices include using data from the accelerometer and/or gyroscope to condition the data provided by the intraoral PPG sensor. The conditioning of the data is done to filter out irrelevant data or, said differently, filtering in relevant data. More specifically, as an example, the one or more accelerometer and/or gyroscope sensors can be used to measure head movements and body vibrations of the wearer. The head movements and body vibrations can be used as indicators of the wearer's sleep state (e.g. awake, REM sleep, light sleep, deep sleep). Similarly, the head movements and body vibrations of the wearer may then be used to extrapolate restless leg syndrome and other movement-based sleep disorders. The one or more accelerometer and/or gyroscope sensors may also be used to detect high frequency jerk-lie movements that signal restless limbs syndrome or other myoclonic (involuntary) muscle activity during sleep. An intraoral photoplethysmogram (PPG) sensor may be used to measure blood O2 levels and heart rate may further provide basic data to extract respiratory rate and blood pressure. The PPG sensor working principle is based on two light sources having distinct wavelengths emitting light and a photodiode measuring the reflected and the transmitted light. A Fourier transform in the time domain of the variation of optical intensity of the detected light may be used to show the peaks of the PPG signals. The difference between two consecutive peaks determines the heart-rate value. The PPG sensor is sensitive to motion and may produce data contaminated or corrupted by the user's movements. The data provided by the accelerometer and/or gyroscope may be used to eliminate the effect of body movements of the user in the data produced by the PPG sensor. The ensuing data provide desired characteristics of the user's blood O2 levels, heart rate, etc.

The pulse transit time (PTT) working principle is based on two sources, able to emit and detect signals. The sources may be light sources, ultrasonic sources, etc. In the context of this embodiment, the light sources and the photodiode used are the sources and the photodiode of the PPG sensor. The light sources are positioned at distinct locations such that their relative distance is known. Skilled persons will readily acknowledge that position of the sources could be modified as long as their relative distance is not changed a without affecting the teachings of the present invention. As the optical intensity of the detected light depends on the blood flow, the optical intensity of the detected light from two pulses emitted at distinct times may vary as the blood flow changes between two heart beats. The variation of optical intensity of the detected light with the intraoral PPG sensor allows to determine the average flow velocity of the blood. From the average flow velocity, it is possible to indirectly measure or determine the blood pressure within an expected margin of error (e.g., based on statistical analysis and/or mathematical predictions). Thus, the blood pressure is computed using a PTT method and the data from an intraoral PPG sensor.

A method is generally conceived to be a self-consistent sequence of steps leading to a desired result. These steps require physical manipulations of physical quantities. Usually, though not necessarily, these quantities take the form of electrical or magnetic signals capable of being stored, transferred, combined, compared, and otherwise manipulated. It is convenient at times, principally for reasons of common usage, to refer to these signals as bits, values, parameters, items, elements, objects, symbols, characters, terms, numbers, or the like. It should be noted, however, that all of these terms and similar terms are to be associated with the appropriate physical quantities and are merely convenient labels applied to these quantities.

The description of the present invention has been presented for purposes of illustration but is not intended to be exhaustive or limited to the disclosed embodiments. Many modifications and variations will be apparent to those of ordinary skill in the art. The embodiments were chosen to explain the principles of the invention and its practical applications and to enable others of ordinary skill in the art to understand the invention in order to implement various embodiments with various modifications as might be suited to other contemplated uses. The drawings are not necessarily drawn to scale.

What is claimed is:

1. An intraoral sleep monitoring system comprising:

an intraoral sleep monitoring device comprising:

an intraoral frame conforming in shape to an interior of a mouth of a user and configured to be removably attached to a dental arch of the mouth; and an intraoral network interface module;

a wristband, configured to wirelessly communicate with the intraoral network interface module, comprising:

a wristband frame configured to be removably attached to a wrist of the user;

one or more electronics-compatible substrate comprising:

at least one intraoral substrate supported by the intraoral frame; and at least one wristband substrate supported by the wristband frame;

one or more measurement device, mounted on the one or more electronics-compatible substrate, comprising:

a photoplethysmogram (PPG) sensor mounted on the intraoral substrate and configured to generate a PPG signal in real time from within the mouth; and an accelerometer and/or gyroscope sensor, mounted on the wristband substrate and configured to generate movement data of the user in real time; and a processor connected with the photoplethysmogram (PPG) sensor and configured to:

receive the movement data from the accelerometer and/or gyroscope sensor and the PPG signal from the PPG sensor; and process the PPG signal in real time by filtering out movement-related artifacts based on the movement data, thereby producing a filtered PPG signal; and a memory module connected with the processor and configured to:

record dynamic data comprising the filtered PPG signal.

2. The intraoral sleep monitoring system of claim 1, wherein the one or more measurement device further comprises a sound sensor mounted on the at least one intraoral substrate and configured to determine a breathing status of the user by measuring an intraoral noise of the user.

3. The intraoral sleep monitoring system of claim 1, further comprising remote storage system configured to receive the dynamic data via the network interface module, and wherein the memory module is limited to a short-term recording of the dynamic data.

4. The intraoral sleep monitoring system of claim 1, wherein the intraoral frame comprises a retention mechanism configured to fasten the intraoral sleep monitoring device to teeth of the user as an occlusal splint.

5. The intraoral sleep monitoring system of claim 1, wherein the intraoral frame comprises a retention mechanism configured to fasten the intraoral sleep monitoring device to teeth of the user as a palatal base plate with metal clasps.

6. The intraoral sleep monitoring system of claim 1, wherein the intraoral frame is produced using a single compound by additive manufacturing or by milling.

7. The intraoral sleep monitoring system of claim 1, wherein the PPG sensor is in wireless communication with the processor.

* * * * *